United States Patent
Wong et al.

(10) Patent No.: US 10,369,127 B2
(45) Date of Patent: **\*Aug. 6, 2019**

(54) METHOD FOR INHIBITING THE EXPRESSION OF ABC TRANSPORTER PROTEIN

(71) Applicant: Macau University of Science and Technology, Taipa (MO)

(72) Inventors: Kam Wai Wong, Taipa (MO); Yuen Kwan Law, Taipa (MO); Man Chung Wong, Taipa (MO)

(73) Assignee: MACAU UNIVERSITY OF SCIENCE AND TECHNOLOGY, Taipa (MO)

( * ) Notice: Subject to any disclaimer, the term of this patent is extended or adjusted under 35 U.S.C. 154(b) by 0 days.

This patent is subject to a terminal disclaimer.

(21) Appl. No.: 15/632,738

(22) Filed: Jun. 26, 2017

(65) Prior Publication Data

US 2018/0050045 A1   Feb. 22, 2018

Related U.S. Application Data

(63) Continuation-in-part of application No. 15/242,883, filed on Aug. 22, 2016, now Pat. No. 9,895,338.

(30) Foreign Application Priority Data

Aug. 22, 2016   (AU) .................................. 2016101491

(51) Int. Cl.
| | | |
|---|---|---|
| A61K 31/28 | (2006.01) | |
| A61K 31/555 | (2006.01) | |
| A61K 45/06 | (2006.01) | |

(52) U.S. Cl.
CPC ............ *A61K 31/28* (2013.01); *A61K 31/555* (2013.01); *A61K 45/06* (2013.01)

(58) Field of Classification Search
CPC ............................. A61K 31/28; A61K 31/555
USPC ....................................................... 514/188
See application file for complete search history.

(56) References Cited

PUBLICATIONS

Dawid, Urzsula, Przemysl Chenniczny (2011), vol. 90(2), pp. 174-179. (Year: 2011).*
Amiri-Kordestani, Drug Resist Updat (2012), vol. 15(0), pp. 50-61. (Year: 2012).*
Szakacs et al, Chemical Reviews (2014), vol. 114, pp. 5753-5774. (Year: 2014).*
Abdallah et al, J. Advanced Research (2015), vol. 6, pp. 45-62. (Year: 2015).*
Anderson, Chem and Biology (2003), vol. 10, pp. 787-797. (Year: 2003).*

(Continued)

*Primary Examiner* — Craig D Ricci
*Assistant Examiner* — Janet L Coppins
(74) *Attorney, Agent, or Firm* — Renner Kenner Greive Bobak Taylor & Weber

(57) ABSTRACT

A method for inhibiting the expression and/or functional activity of an ABC transporter protein in a subject suffering from a disorder associated with an overexpression of the ABC transporter protein includes administrating a cobalt-polypyridyl complex to the subject. A method for inhibiting the expression and/or functional activity of an ABC transporter in cells includes contacting the cells with an effective amount of the cobalt-polypyridyl complex.

15 Claims, 11 Drawing Sheets

(56) References Cited

PUBLICATIONS

Thiel, Nature Biotechnology (2004), vol. 2, pp. 513-519. (Year: 2004).*
Feldt et al. J. of American Chem Society (2010), vol. 132, pp. 16714-16724. (Year: 2010).*
M. Frezza, S. Hindo, D. Chen, A. Davenport, S. Schmitt, D. Tomco, and Q. P. Dou, "Novel Metals and Metal Complexes as Platforms for Cancer Therapy", Current Pharmaceutical Design, 2010, 16, pp. 1813-1825.
S. Dasari and P. B. Tchounwou, "Cisplatin in cancer therapy: Molecular mechanisms of action", Eur J Pharmacol (2014), http://dx.doi.org/10.1016/j.ejphar.2014.07.025.
I. Ott, "On the medicinal chemistry of gold complexes as anticancer drugs", Coordination Chemistry Reviews 253 (2009) pp. 1670-1681.
S. Nobili, E. Mini, I. Landini, C. Gabbiani, A. Casini, and L. Messori, "Gold Compounds as Anticancer Agents: Chemistry, Cellular Pharmacology, and Preclinical Studies", Medicinal Research Reviews, vol. 30, No. 3, pp. 550-580, 2010.
I. Romero-Canelon and P. J. Sadler, "Next-Generation Metal Anticancer Complexes: Multitargeting via Redox Modulation", Inorganic Chemistry, 2013, 52, pp. 12276-12291.
K. Suntharalingam, W. Lin, T. C. Johnstone, P. M. Bruno, Y-R. Zheng, M. T. Hemann, and S. J. Lippard, "A Breast Cancer Stem Cell-Selective, Mammospheres-Potent Osmium(VI) Nitrido Complex", J. Amer. Chem. Soc., 2014, 136, pp. 14413-14416.
T. Zou, C. T. Lum, C-N. Lok, J-J. Zhang, and C-M. Che, "Chemical biology of anticancer gold(III) and gold(I) complexes", Chem Soc Rev, 2015, 44, pp. 8786-8801.
A. A. Jensen and F. Tuchsen, "Cobalt Exposure and Cancer Risk", Crit Rev Toxicol, 1990, 20, pp. 427-439.
M. C. Heffern, N. Yamamoto, R. J. Holbrook, A. L. Eckermann, and T. J. Meade, "Current Opinion in Chemical Biology", 2013, 17, pp. 189-196.
T. Takeuchi, A. Bottcher, C. M. Quezada, M. I. Simon, T. J. Meade, and H. B. Gray, "Selective Inihibition of Human a-Thrombin by Cobalt(III) Schiff Base Complexes", J. Amer. Chem. Soc. 1998, 120, pp. 8555-8556.
A. S. Harney, J. Lee, L. M. Manus, P. Wang, D. M. Ballweg, C. Labonne, and T. J. Meade, "Targeted inhibition of Snail family zinc finger transcription factors by oligonucleotide-Co(III) Schiff base conjugate", PNAS, 2009, vol. 106, No. 33, pp. 13667-13672.
M. D. Peterson, R. J. Holbrook, T. J. Meade, and E. A. Weiss, "Photoinduced Electron Transfer from PbS Quantum Dots to Cobalt(III) Schiff Base Complexes: Light Activation of a Protein Inhibitor", J. Amer. Chem. Soc., 2013, 135, pp. 13162-13167.
D. Luis, J. Silva, A. Tomaz, R. De Almeida, M. Larguinho, P. Baptista, L. Martins, T. Silva, P. Borralho, C. Rodrigues, A. Rodrigues, A. Pombeiro and A. Fernandes, "Insights into the mechanisms underlying the antiproliferative potential of a Co(II) coordination compound bearing 1,10-phenanthroline-5,6-dione: DNA and protein interaction studies", J. Biol. Inorg. Chem. (2014) 19, pp. 787-803.
G. Vignesh, R. Senthilkumar, P. Paul, V. S. Periasamy, M. A. Akbarsha, and S. Arunachalam, "Protein binding and biological evaluation of a polymer-anchored cobalt(III) complex containing a 2,2'-bipyridine ligand", RSC Adv., 2014, 4, pp. 57483-57492.
S. M. Feldt, E. A. Gibson, E. Gabrielsson, L. Sun, G. Boschloo, and A. Hagfeldt, "Design of Organic Dyes and Cobalt Polypyridine Redox Mediators for High-Efficiency Dye-Sensitized Solar Cells", J. Amer. Chem. Soc. 2010, 132, pp. 16714-16724.
B. M. Klahr and T. W. Hamann, Performance Enhancement and Limitations of Cobalt Bipyridyl Redox Shuttles in Dye-Sensitized Solar Cells, J. Phys. Chem. C 2009, 113, pp. 14040-14045.
Y. Xie and T. W. Hamann, "Fast Low-Spin Cobalt Complex Redox Shuttles for Dye-Sensitized Solar Cells", J. Phys. Chem. Lett., 2013, 4, pp. 328-332.
H-S. Kim, S-B. Ko, I-H. Jang, and N-G. Park, "Improvement of mass transport of the [Co(byp)3]II/III redox couple by controlling nanostructure of TiO2 films in dye-sensitized solar cells", Chem. Commun, 2011, 47, pp. 12637-12639.
Z. Sun, M. Liang, and J. Chen, "Kinetics of Iodine-Free Redox Shuttles in Dye-Sensitized Solar Cells: Interfacial Recombination and Dye Regeneration", Acc. Chem. Res., 2015, 48, pp. 1541-1550.
V. Wong, T. Li, B. Law, E. Ma, N. Yip, F. Michelangeli, C. Law, M. Zhang, K. Lam, P. Chan, and L. Liu, "Saikosaponin-d, a novel SERCA inhibitor, induces autophagic cell death in apoptosis-defective cells", Cell Death and Disease (2013) 4, e720; doi: 10.1038/cddis.2013.217.
V. Wong, H. Dong, X. Liang, L-P. Bai, Z-H. Jiang, Y. Guo, A-N. Kong, R. Wang, R. Kam, B. Law, W. Hsiao, K. Chan, J. Wang, R. Chan, J. Guo, W. Zhang, F. Yen, H. Zhou, E. Leung, Z. Yu and L. Liu, Rh2E2, a novel metabolic suppressor, specifically inhibits energy-based metabolism of tumor cells, Oncotarget, vol. 7, No. 9, pp. 9907-9924.

* cited by examiner (Continued) Effects of cobalt-polypyridyl complex of Formula (IV) in HCT-8 taxol-resistant colon cancer cells (Continued) Effects of cobalt-polypyridyl complex of Formula (IV) in A549 taxol-resistant lung cancer cells

METHOD FOR INHIBITING THE EXPRESSION OF ABC TRANSPORTER PROTEIN

TECHNICAL FIELD

The present invention relates in a first aspect to a method for inhibiting the expression and/or functional activity of an ABC transporter protein in a subject in particular a subject suffering from a disorder associated with an overexpression of the ABC transporter protein. In another aspect of the present invention, the invention relates to a method for inhibiting the expression and/or functional activity of the ABC transporter protein in cells by contacting the cells with a cobalt-polypyridyl complex.

BACKGROUND OF THE INVENTION

Cancer is still a life-threatening disease affecting an increasing number of people in the world. Platinating compounds including cisplatin, carboplatin, and oxaliplatin are common chemotherapeutic compounds used for treating cancer. However, a significant number of patients have acquired or develop resistance to these chemotherapeutic compounds after initial therapeutic treatments. Such drug-resistance in cancer is the major impediment to a successful treatment. Such cells display a reduced sensitivity to chemotherapeutic compounds based on several mechanisms in particular including an increase in drug efflux such as by an increased expression or activity of ABC transporter proteins such as P-glycoprotein (P-gp, MDR1, or ABCB1) or affected apoptosis pathways such as by mutated or dysfunctionally regulated genes and respective proteins. For example, cancer cells lacking cell death mediators Bax and Bak have been reported to develop drug-resistance and the high frequency of p53 mutations is expected to lead to a drug resistance of cancer cells, too.

Studies also revealed that ABC transporter protein, in particular P-glycoprotein, acts as a major barrier to drug treatment in various diseases due to its high expression in cells and/or tissues. In addition to cancer, the diseases showing ABC-protein-dependent drug resistance include fungal infections, bacterial infections, AIDS, CNS diseases such as Alzheimer's disease and epilepsy, congestive heart failure, etc. It is believed that the alternation of functional activity of P-glycoprotein in a subject is a way to improve and/or optimize therapeutic efficacy of a treatment in said subject.

Therefore, different approaches have been applied to identify novel therapeutic agents, molecular mechanisms and targets for treating cancer which are also suitable to overcome drug resistance. It is also believed that a therapeutic agent being effective in inhibiting the expression of ABC transporter proteins such as P-glycoprotein may also be suitable in treating a subject suffering a disorder associated with an altered expression or overexpression of the ABC transporter protein.

Transition metal ions are essential for the proper functions of organisms; examples including copper, iron, and manganese ions work with proteins and enzymes for multiple biological processes such as electron transfer and catalysis. As metals are involved in redox activity, coordination, and reactivity towards organic substrates in organisms, and are tightly regulated under normal conditions, aberrant metal ion concentrations are associated with pathogenesis of diseases, in particular of cancers. For instance, enriched copper ions found in cancer tissues are suggested to promote the angiogenesis processes in tumors.

In fact, metal-containing compounds have been used to treat a wide range of diseases. For example, cisplatin (cis-[PtII(NH$_3$)$_2$Cl$_2$]) can bind to the purine bases of the DNA, thereby led to DNA damage resulting in apoptosis in cancer cells. However, due to severe side effects such as dose-dependent toxicity, allergy, effects on the kidneys and immunity, gastrointestinal disorders, hemorrhage and loss of hearing, the clinical use of cisplatin is limited. Acquired resistance to cisplatin is caused by an increased efflux or detoxification of the drug, increased rate of DNA repair, as well as a reduced susceptibility of cancer cells in response to drug-induced cell death. Other platinum-containing anti-cancer analogs such as carboplatin and oxaliplatin are therefore used as alternative to cisplatin and further transition metal complexes including zinc(II), copper(II), gold(III), copper chelating agents, and non-platinum metal complexes such as ruthenium-containing compounds were studied for their potential as anti-cancer agents, too.

The exploration and exploitation of other non-platinum anti-cancer drugs have received considerable attention. In view of the fact that soluble cobalt salts can adversely interfere with cell division and bind to nucleic acids inside the cell nucleus, one may postulate that cobalt complexes could work as anti-cancer agents like platinum-containing analogs. However, they were also reported for being weakly mutagenic and inducing metastasis in animal models (Jensen A. A. and Tuchsen F., Crit Rev Toxicol, 1990, 20, 427-437). There have been some examples of cobalt(III) complexes with equatorial tetradentate Schiff base ligands as potent inhibitors of a wide range of zinc-dependent proteins (Heffern, M. C. et al., Curr Opin Chem Biol, 2013, 17, 189-196, Takeuchi, T. et al., J. Am. Chem. Soc., 1998, 120, 8555-8556, Harney, A. S. et al., Proc Natl Acad Sci USA, 2009, 106, 13667-13672, Peterson, M. D, J Am Chem Soc, 2013, 135, 13162-13167), however, the related use of cobalt pyridine complexes in biological applications or specifically for the development of anti-cancer drugs remains substantially unexplored (Luis, D. V. et al., J Biol Inorg Chem, 2014, 19, 787-803, Vignesh, G. et al., Rsc Advances, 2014, 4, 57483-57492). On the other hand, cobalt(II)/(III) complexes with pyridine ligands have recently been developed as redox mediators in dye-sensitized solar cells (DSCs) (Feldt, S. M., et al., J Am Chem Soc, 2010, 132, 16714-16724, Klahr, B. M. and Hamann, T. W., J Phys Chem C, 2009, 113, 14040-14045, Xie, Y. and Hamann, T. W., J Phys Chem Lett, 2013, 4, 328-332, Kim, H. S. et al., Chem Commun (Camb), 2011, 47, 12637-12639, Sun, Z. et al., Acc Chem Res, 2015, 48, 1541-1550), but not in the field of cancer treatment or the specific treatment of multidrug-resistant cancer.

Although there has been increased research in this regard, there remains a strong need for methods and means allowing for an effective therapeutic treatment of cancer, especially of multidrug-resistant cancer and cancer cells with a multidrug-resistant phenotype, respectively. Also, efficacious treatment options are urgently required for specifically treating subjects with a disorder associated with an overexpression of ABC transporter proteins.

SUMMARY OF THE INVENTION

The present invention relates in a first aspect to a method for inhibiting the expression and/or functional activity of an ABC transporter protein in a subject suffering from a disorder associated with an overexpression of the ABC transporter protein, in particular an overexpression of P-glycoprotein. The method comprises the step of administering an effective amount of a cobalt-polypyridyl complex of Formula (II) to the subject:

Formula (II)

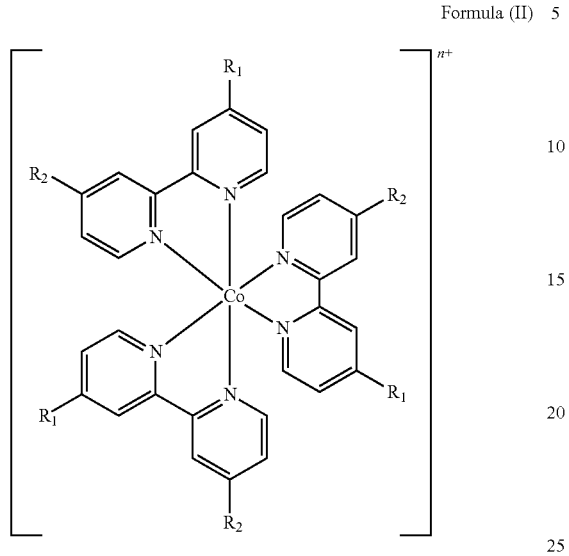

wherein $R_1$ and $R_2$ are identical and selected from —H, —$CH_3$, —$C_9H_{19}$ or —$OCH_3$ and wherein n is 2 or 3.

In an embodiment, the disorder is multidrug-resistant ABC-protein-dependent cancer against at least taxol, and the cancer may be breast cancer, lung cancer or colon cancer.

In an embodiment, the disorder is selected from the group consisting of a CNS disease, an autoimmune disease, a fungal infection, a bacterial infection, a cardiovascular disease and AIDS. Preferably, the disorder is epilepsy or rheumatoid arthritis.

In particular, the effective amount of cobalt-polypyridyl compound is administered to said subject for inhibiting the expression and/or functional activity of P-glycoprotein.-

The cobalt-polypyridyl complex administered according to the present invention comprises a structure of Formula (II) and optionally a counterion:

Formula (II)

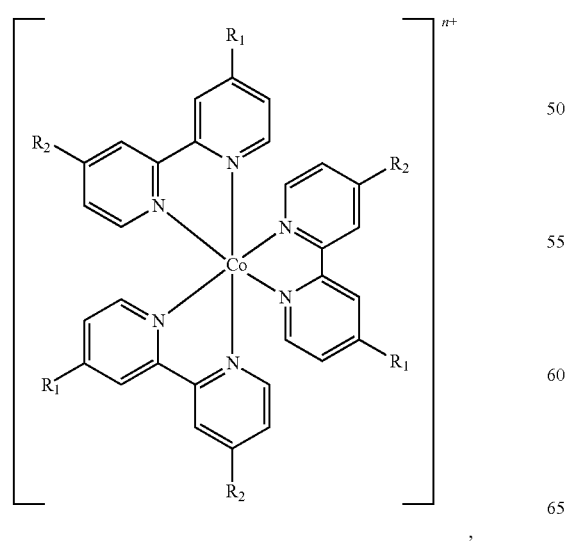

wherein $R_1$ and $R_2$ are identical and selected from —H, —$CH_3$, —$C_9H_{19}$ or —$OCH_3$ and wherein n is 2 or 3, i.e. the cobalt-polypyridyl complex comprises a structure selected from Formula (III), (IV) or (V):

Formula (III)

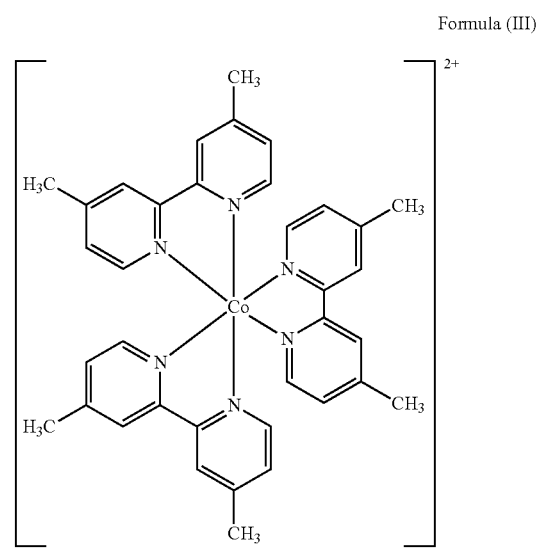

,

Formula (IV)

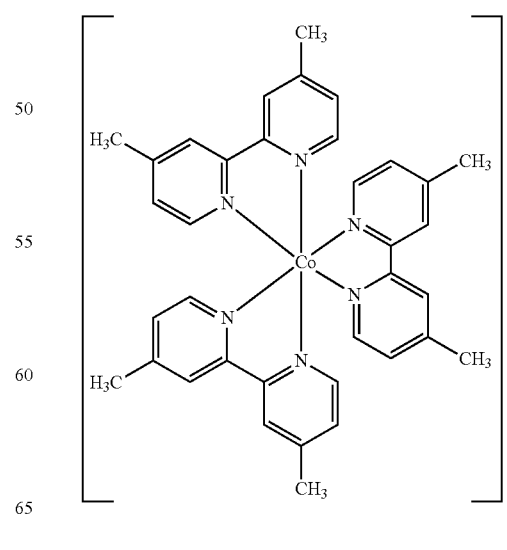

, or

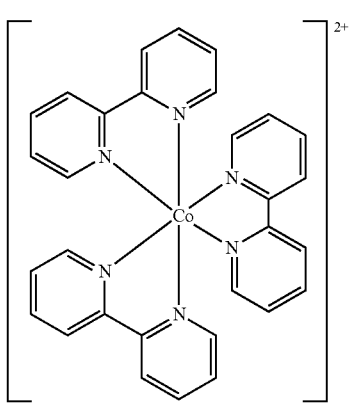

Formula (V)

Preferably, the cobalt-polypyridyl complex comprises a structure of Formula (IV):

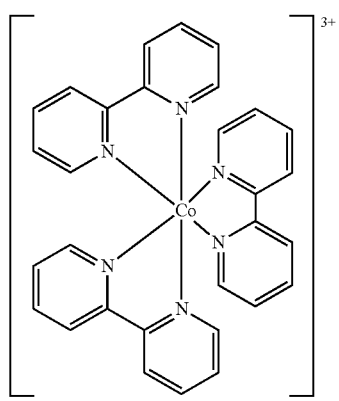

Formula (VI)

The cobalt-polypyridyl complex of the present invention may be administered in combination with at least one further chemotherapeutic compound, in particular selected from the group consisting of a topoisomerase-II inhibitor, an anthracycline, a coordination complex of platinum, a taxane, a protein kinase inhibitor, a vinca alkaloid or derivative thereof, a topoisomerase-I inhibitor and a nucleotide analog or precursor analog. Alternatively or additionally, the cobalt-polypyridyl complex of the present invention may be administered in combination with radiotherapy and/or immunotherapy.

According to the invention is also the cobalt-polypyridyl complex described above for use as a medicament for the treatment of a disorder associated with an overexpression of the ABC transporter protein, in particular P-glycoprotein-dependent disorder such as P-glycoprotein-dependent multidrug-resistant cancer, via inhibition of P-glycoprotein. Another aspect of the invention refers to the use of the cobalt-polypyridyl complex described above for preparing a medicament for said treatment.

The present invention further provides a method for inhibiting the expression and/or functional activity of an ABC transporter protein in cells by contacting the cells with an effective amount of a cobalt-polypyridyl complex, wherein the cobalt-polypyridyl complex comprises a structure of Formula (II):

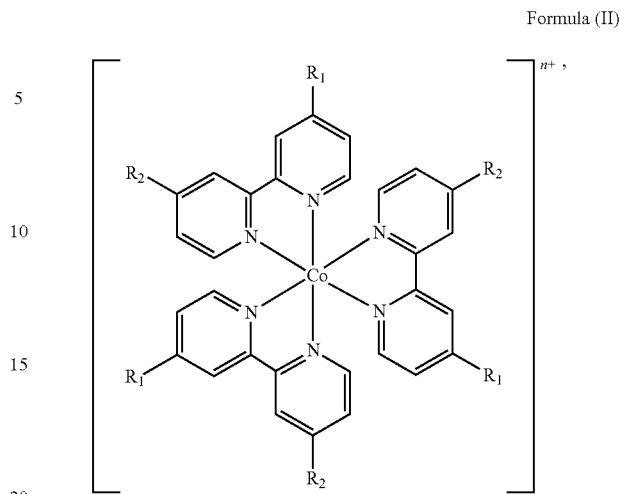

Formula (II)

wherein $R_1$ and $R_2$ are identical and selected from —H, —$CH_3$, —$C_9H_{19}$ or —$OCH_3$ and wherein n is 2 or 3.

Preferably, the cobalt-polypyridyl complex as described above interacts with the ABC transporter protein directly or indirectly to inhibit the expression and/or functional activity of the ABC transporter protein in cells where it overly expressed. In particular, the expression and/or functional activity of P-glycoprotein of the cells is suppressed. The cells of said method may be multidrug-resistant cells and may be ABC-protein-dependent. In an embodiment, the cells are multidrug-resistant cancer cells, preferably with an overexpression of the ABC transporter protein, against at least taxol, and the cancer cells may be breast cancer cells, lung cancer cells or colon cancer cells.

The present invention also provides a kit comprising an effective dose of the cobalt-polypyridyl complex as described above and an effective dose of at least a further chemotherapeutic compound commonly used for treating cancer, namely selected from the group consisting of a topoisomerase-II inhibitor, an anthracycline, a coordination complex of platinum, a taxane, a protein kinase inhibitor, a vinca alkaloid or derivative thereof, a topoisomerase-I inhibitor and a nucleotide analog or precursor analog. The kit may further comprise excipients, in particular pharmaceutically acceptable excipients, such as a carrier, salt, buffer, water, or a combination thereof.

DESCRIPTION OF THE EMBODIMENTS

Figure 1A:
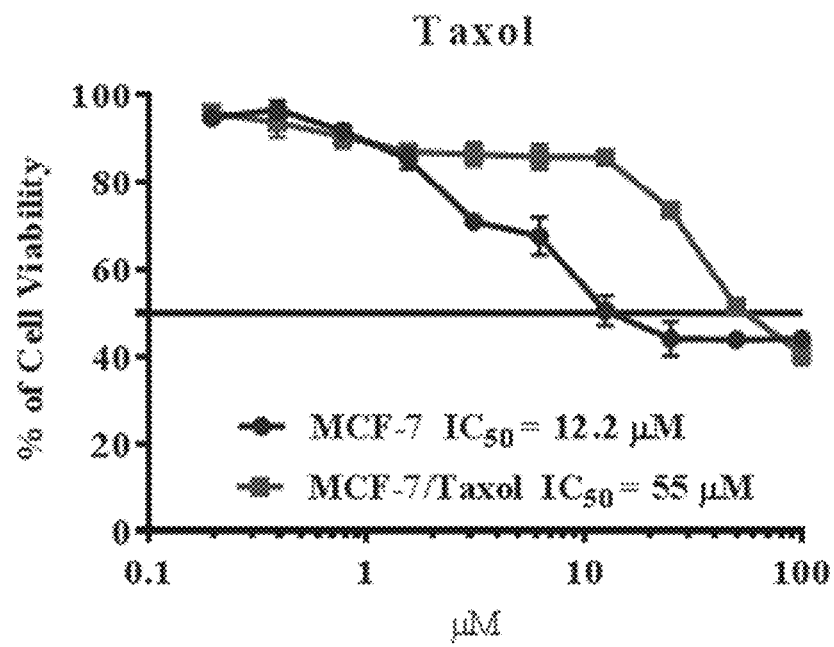
FIG. 1A is a diagram showing the percentage of cell viability of taxol-resistant MCF-7 breast cancer cells after the treatment with the cobalt-polypyridyl complex of Formula (IV) with $PF_6^-$ as counterion and in the control group.

The following preparations and examples are given to enable those skilled in the art to more clearly understand and to practice the present invention. They should not be considered as limiting the scope of the invention, but merely as being illustrative and for representing preferred embodiments thereof. The technical terms used in the present patent application have the meaning as commonly understood by a respective skilled person unless specifically defined otherwise.

As used herein, "comprising" means including the following elements or structures but not excluding others. "Essentially consisting of" means that the material or compound consists of the respective element or structure along with usually and unavoidable impurities such as side products and components usually resulting from the respective preparation or method for obtaining the material such as traces of further components or solvents. "Consisting of" means that the material solely consists of, i.e. is formed by the respective element. As used herein, the forms "a", "an", and "the" are intended to include the singular and plural forms unless the context clearly indicates otherwise.

The present invention relates in a first aspect to a method for inhibiting the expression and/or functional activity of an ABC transporter protein, in particular P-glycoprotein, in a subject suffering from a disorder associated with an overexpression of the ABC transporter protein. In an embodiment, the disorder is a cancer where the ABC transporter protein is overly expressed. In another embodiment, the disorder is selected from the group consisting of a CNS disease, an autoimmune disease, a fungal infection, a bacterial infection, a cardiovascular disease and AIDS. The disorder may be epilepsy or rheumatoid arthritis. Said method comprises the step of administering an effective amount of a cobalt-polypyridyl complex to said subject.

The term "cobalt-polypyridyl complex" as used herein means a complex, i.e. a compound, formed by a cobalt ion and polypyridyl ligands including at least one of Formula (I) with $R_1$ and $R_2$ as described below and optionally comprising a counterion. Thus, the cobalt-polypyridyl complex does not comprise non-polypyridyl ligands or non-polypyridyl polymers. A polypyridyl ligand generally means a ligand having at least two pyridine rings covalently linked to each other, which may together form a larger ring system. Polypyridine ligands include, in particular, bipyridine, terpyridine and phenanthroline. The pyridine rings may optionally be substituted, in particular with alkyl or alkoxy groups such as $C_1$-$C_{10}$ alkyl or $C_1$-$C_{10}$ alkoxy groups. The cobalt-polypyridyl complex of the present invention comprises at least one polypyridyl ligand of Formula (I):

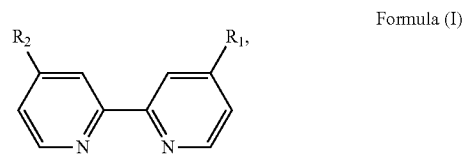

Formula (I)

which is a bidentate ligand and wherein $R_1$ and $R_2$ are independently selected from hydrogen, a $C_1$-$C_{10}$ alkyl or a $C_1$-$C_{10}$ alkoxy, preferably from hydrogen, a $C_1$-$C_9$ alkyl or a $C_1$-$C_9$ alkoxy. Preferably, $R_1$ and $R_2$ are identical and most preferably selected from —H, —CH$_3$, —C$_9$H$_{19}$ or —OCH$_3$.

The term "$C_1$-$C_{10}$ alkyl" as used in the present invention refers to a hydrocarbyl radical having from 1 to 10 carbon atoms which includes a straight chain or branched alkyl group. Namely, it comprises, for example, methyl, ethyl, propyl, isopropyl, nonyl and so on. "$C_1$-$C_{10}$ alkoxy" refers to a radical having a formula -AB wherein A is an oxygen atom and B is $C_1$-$C_{10}$ alkyl, i.e. a straight chain or branched alkyl group with 1 to 10 carbon atoms, including for example methoxy and ethoxy.

Preferably, the cobalt-polypyridyl complex comprises three ligands of Formula (I) coordinated to one cobalt ion, i.e. the cobalt-polypyridyl complex is a cobalt tris(bipyridine) system. The cobalt ion is preferably of the oxidation state +2 or +3. The cobalt ion is preferably octahedrally coordinated. In an octahedral coordination geometry, the ligands are coordinated to the cobalt ion in a symmetrical distribution, leading to the formation of an octahedron.

A counterion might affect the solubility or other chemical or physical properties of the cobalt-polypyridyl complex, wherein the exact nature of the counterion is not critical as long as it is pharmaceutically acceptable and/or not significantly toxic in the amounts used. Counterions can in particular be anions which are unlikely to bind directly to the cobalt ion of the cobalt-polypyridyl complex, i.e. non-coordinating anions. Non-coordination anions include, for example, hexafluorophosphate ($PF_6^-$), perchlorate ($ClO_4^-$) or tetrafluoroborate ($BF_4^-$). Examples of counterions, in particular, include hexafluorophosphate ($PF_6^-$) or chloride ($Cl^-$).

The term cobalt-polypyridyl complex encompasses any diastereomers and their mixtures, enantiomers and their mixtures such as racemates and salts of the cobalt-polypyridyl complex, in particular pharmaceutically acceptable salts. The skilled person is aware of such terms and how to isolate specific diastereomers or enantiomers. Likewise, the term cobalt-polypyridyl complex encompasses any solvates or hydrates of the cobalt-polypyridyl complex. The term "solvate" refers to a complex of variable stoichiometry formed by a solute, i.e. the cobalt-polypyridyl complex, and a solvent. If the solvent is water, the solvate formed is a hydrate.

Preferably, the cobalt-polypyridyl complex of the present invention comprises a structure of Formula (II) and optionally a counterion:

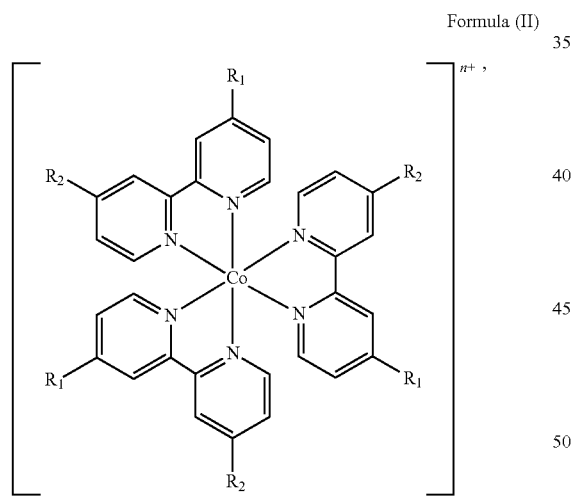

Formula (II)

wherein $R_1$ and $R_2$ are identical and selected from —H, —$CH_3$, —$C_9H_{19}$ or —$OCH_3$ and wherein n corresponds to the oxidation state of the cobalt ion and is preferably 2 or 3. Preferably $R_1$ and $R_2$ are selected from —H, —$CH_3$, —$C_9H_{19}$ or —$OCH_3$. The counterion is preferably a monovalent anion and selected from hexafluorophosphate ($PF_6^-$) or chloride ($Cl^-$).

More preferably, the cobalt-polypyridyl complex comprises and in particular essentially consists of a structure of one of Formulas (III), (IV), (V), (VI), (VII) or (VIII) and optionally a counterion, in particular a monovalent counterion selected from hexafluorophosphate ($PF_6^-$) or chloride ($Cl^-$):

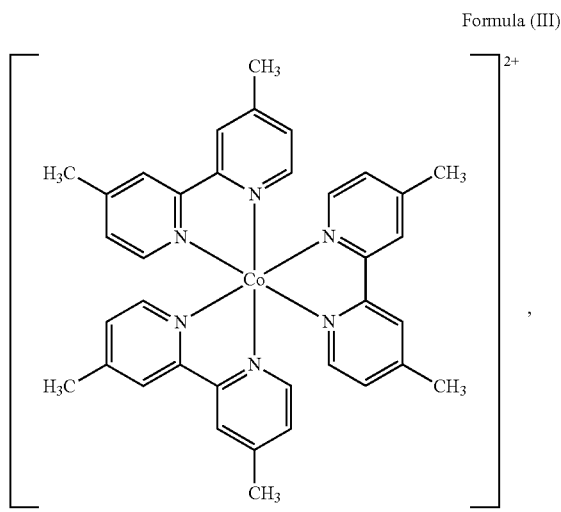

Formula (III)

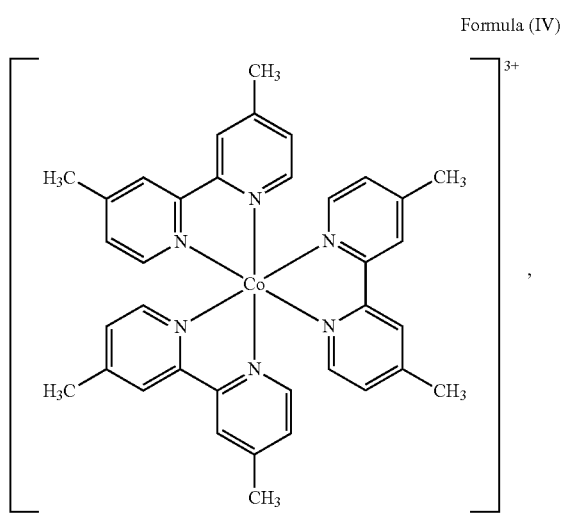

Formula (IV)

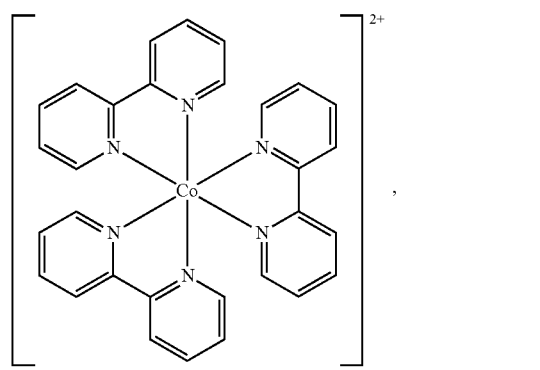

Formula (V)

Formula (VI)

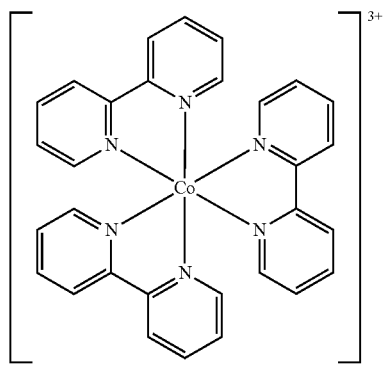

Formula (VII)

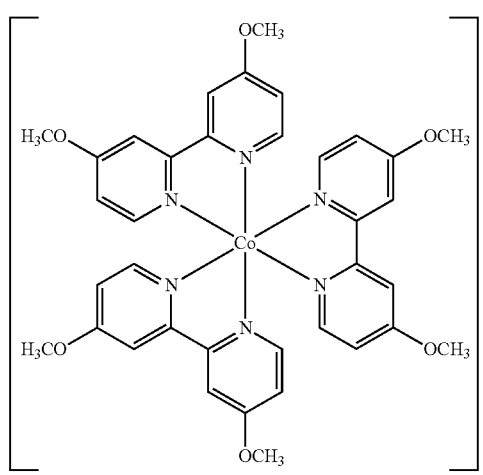

, or

Formula (VIII)

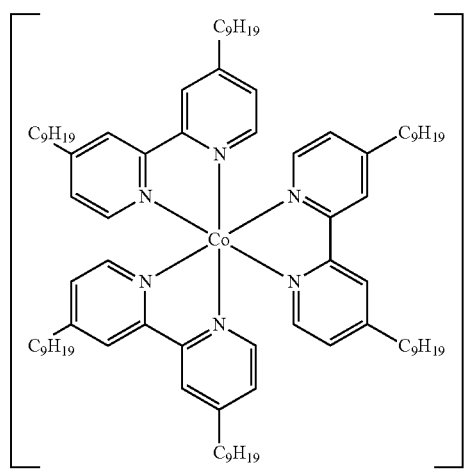

.

Formula (III)

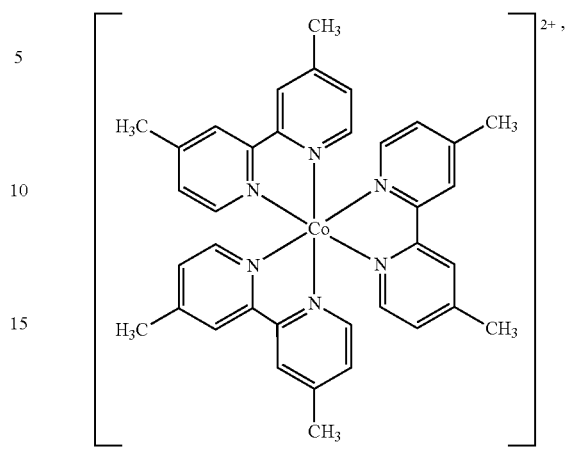

,

Formula (IV)

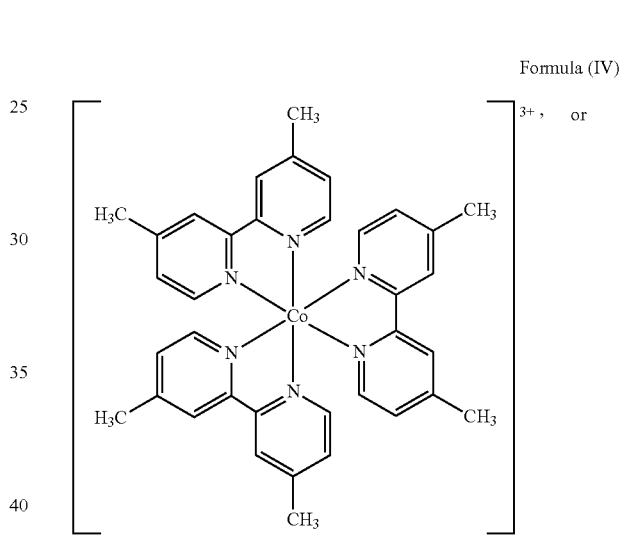

$3+$, or

Formula (VII)

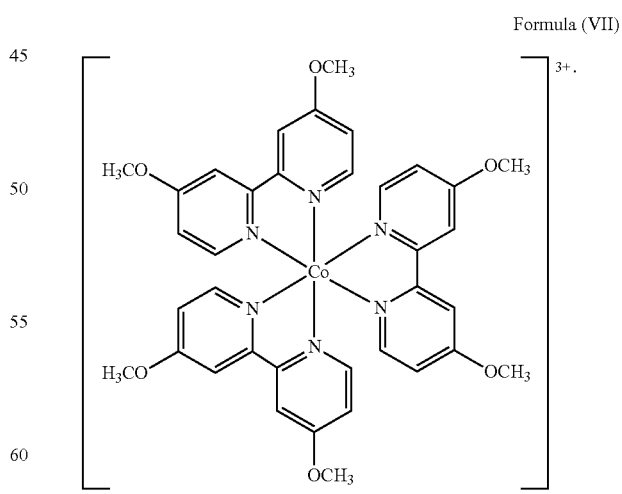

$3+$.

In further preferred embodiments, the cobalt-polypyridyl complex comprises and in particular essentially consists of a structure selected from Formula (III), Formula (IV) or Formula (VII) and optionally a counterion:

In most preferred embodiments of the present invention, the cobalt-polypyridyl complex comprises and in particular essentially consists of a structure of Formula (IV) and optionally a counterion:

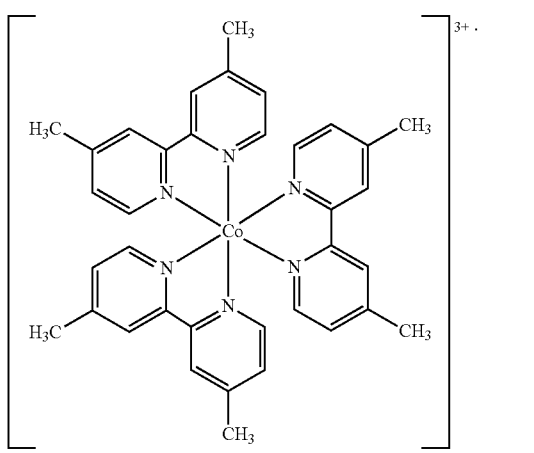

Formula (IV)

In particular embodiments of the present invention, the cobalt-polypyridyl complex comprises and in particular essentially consists of a structure of Formula (IV) and a counterion, wherein the counterion is a monovalent anion and preferably selected from hexafluorophosphate ($PF_6^-$) or chloride ($Cl^-$).

The cobalt-polypyridyl complex may be administered in the method of the present invention in combination with:
(ii) an effective amount of at least one chemotherapeutic compound, which chemotherapeutic compound is a compound selected from the group consisting of a topoisomerase-II inhibitor, an anthracycline, a coordination complex of platinum, a taxane, a protein kinase inhibitor, a vinca alkaloid or derivative thereof, a topoisomerase-I inhibitor and a nucleotide analog or precursor analog;
(ii) radiotherapy, and/or
(iii) immunotherapy.

The expression "effective amount" and "effective dose" generally denote an amount sufficient to produce therapeutically desirable results, wherein the exact nature of the result varies depending on the specific disorder which is treated. When the disorder is cancer, the result is usually an inhibition or suppression of the proliferation of the cancer cells, a reduction of cancerous cells or the amelioration of symptoms related to the cancer cells. When the disorder relates to an overexpression and/or enhanced functional activity of ABC transporter protein in cells such as a CNS disease, the results is an inhibition or suppression of the expression and/or functional activity of the ABC transporter protein which may thereby triggering a reduction of the associated cells and/or reducing the ABC transporter protein efflux, e.g. P-glycoprotein efflux. In embodiments, the reduction in P-glycoprotein efflux further facilitates the uptake of at least one convention therapeutic agent to the target cells and/or tissue of the subject.

The effective amount of the cobalt-polypyridyl complex of the present invention may depend on the species, body weight, age and individual conditions of the subject and can be determined by standard procedures such as with cell cultures or experimental animals. A concentration of the cobalt-polypyridyl complex such as the cobalt-polypyridyl complex comprising a structure of Formula (IV) may, for example, be at least 0.5 µM, preferably at least 1 µM, in particular at least 2 µM or at least 5 µM. The subject can be a human or animal, in particular the subject is a mammal, preferably a human. The subject is preferably a human suffering from a disorder associated with an enhanced expression and/or functional activity of an ABC transporter protein in particular P-glycoprotein. In an embodiment, said subject may be suffering from a cancer with a multidrug-resistance. Said subject, thus, includes human subjects having a drug resistance to conventional therapeutic agents which induce cell death in cancer cells, i.e. which are used to treat cancer. In another embodiment, said subject may be suffering from a disorder where the ABC transporter protein is overly expressed and blocks the absorption of a conventional therapeutic agent to the target cells and/or tissues.

The terms "cancer" and "cancerous" refer to or describe a physiological condition in subjects in which a population of cells are characterized by unregulated cell growth.

The term "tumor" simply refers to a mass being of benign (generally harmless) or malignant (cancerous) growth.

The cancer can be of any origin, in particular human origin. In particular, the cancer is selected from the group consisting of:
ovarian cancer,
cervical cancer,
liver cancer,
lung cancer,
breast cancer
gastric cancer, and
colon cancer.

Preferably, the cancer is selected from the group consisting of:
lung cancer,
breast cancer, and
colon cancer.

In particular, the method of the present invention is suitable for treating a subject suffering from cancer. Said cancer is preferably a multidrug-resistant cancer, more preferably a multidrug-resistant ABC-protein-dependent cancer. The provided method is preferably used and particularly effective in treating subjects whose cancer has become "multidrug-resistant". The term "multidrug-resistance" is generally used for an acquired or natural, i.e. intrinsic, resistance of a cancer.

Cancers with cancer cells that have developed resistance to or are naturally resistant to chemotherapeutic compounds, usually to two or more chemotherapeutic compounds, are said to be "multidrug-resistant" in the present patent application such as to chemotherapeutic compounds selected from the group consisting of topoisomerase-II inhibitors, anthracyclines, coordination complexes of platinum, taxanes, protein kinase inhibitors, vinca alkaloids or derivatives thereof, topoisomerase-I inhibitors and nucleotide analogs or precursor analogs. In preferred embodiments of the present invention, the multidrug-resistant cancer is a cancer having multidrug-resistant cancer cells, i.e. cancer cells which have developed resistance to or are naturally resistant to at least one of paclitaxel (taxol), doxorubicin, cisplatin, etoposide and staurosporine, in particular against one of taxol or cisplatin or both of them, more preferably cancer cells that are resistant at least against taxol. In an embodiment of the present invention, the cancer is multidrug-resistant cancer against at least taxol.

A cancer is multidrug-resistant if it comprises cancer cells which are multidrug-resistant, in particular if a significant amount of the cancer cells, such as more than 50%, in said cancer are multidrug-resistant. Accordingly, the multidrug-resistant cancer will be less sensitive or more tolerant to most common chemotherapeutic agents.

A multidrug-resistance can be detected in a subject, cancer, tissue, or cell by administering to the subject, tissue, or cell, compounds such as chemotherapeutic compounds and determining the activity of the chemotherapeutic compounds such as the induction of cell death or the inhibition of the proliferation of cancer cells compared to a reference control, namely cells or tissue of the same cell or tissue type, a cancer or a subject that do not have multidrug-resistance or non-cancerous cells.

The multidrug-resistant cancer preferably has multidrug-resistant cancer cells which are ABC-protein-dependent.

"ABC-protein-dependent", i.e. the multidrug resistance is at least mediated by ABC transporter proteins (hereinafter "ABC-proteins"), in particular by P-glycoprotein, i.e. is associated with an enhanced expression and/or enhanced functional activity of at least one ABC-protein in the multidrug-resistant cancer cells, in particular of P-glycoprotein also referenced as "P-glycoprotein-dependent".

In one embodiment of the present invention, the multidrug-resistance and hence the multidrug-resistant cancer is at least ABC-protein-dependent, in particular P-glycoprotein-dependent.

An enhanced expression and/or enhanced functional activity of at least one ABC-protein, i.e. ABC-protein-dependent multidrug-resistant cancer, means an expression and/or functional activity exceeding, in particular significantly exceeding, the one in normal cells or tissue, i.e. non-cancerous cells or tissue, or cancer cells without the multidrug-resistant phenotype. The term "enhanced expression", "overexpression" or "enhanced functional activity" of at least one ABC-protein such as P-glycoprotein includes embodiments in which the multidrug-resistant cancer cells express the ABC-protein such as P-glycoprotein, whereas in the reference control, i.e. cancer cells without the multidrug-resistant phenotype or non-cancerous cells of the same cell or tissue type, said ABC-protein such as P-glycoprotein is not expressed, at all. That is to say, when said reference control does not express the ABC-protein such as P-glycoprotein, multidrug-resistant cancer cells having a detectable expression or functional activity of the ABC-protein such as P-glycoprotein are ABC-protein-dependent by definition.

Whether a disorder in particular a multidrug-resistant cancer is an ABC-protein-dependent can be determined by methods known to the skilled person in particular comprising immunological methods accompanied by the use of MDR-specific antibodies, immunocytochemistry and immunohistochemistry, respectively, by determining respective mRNA levels such as with Northern blots or quantitative RT-PCR, with MDR-specific antibodies in vivo or with an ABC-protein such as P-glycoprotein efflux assay detecting the efflux of a marker. In particular, an ABC-protein such as P-glycoprotein efflux assay can be used for determining the functional activity of ABC-proteins, i.e. for determining whether multidrug-resistant cancer cells are ABC-protein-dependent. Markers which can be used in said efflux assay include drugs which are a substrate for the respective ABC-protein, a radionuclide or a dye. In particular, a sample of multidrug-resistant cancer cells and, thus, a cancer having those cells, is preferably considered for being ABC-protein-dependent, if it comprises less cells with marker such as dye like Rho123 as revealed by the assay compared to the reference control which is a cell sample with ABC-protein expression as present in cancer cells that do not have a multidrug-resistance phenotype or non-cancerous cells of the same cell or tissue type.

Preferably, an ABC-protein-dependent such as a P-glycoprotein-dependent multidrug-resistant cancer is a cancer comprising multidrug-resistant cancer cells with an expression of ABC-protein or ABC-protein functional activity exceeding the one in the reference control by at least 10%, in particular by at least 20%. For example, the expression or functional activity of P-glycoprotein is at least 10% or at least 20% higher than the expression or functional activity of P-glycoprotein in the reference control.

In an embodiment of the present invention, the multidrug-resistant cancer is a cancer comprising of multidrug-resistant P-glycoprotein-dependent cancer cells, in particular comprising a significant amount of such cancer cells.

As used herein, the disorder associated with an overexpression of the ABC transporter protein refers to a pathological condition associated with an enhanced expression and/or functional activity of the ABC transporter protein. Said disorder may be selected from the group consisting of cancer, a central nervous system (CNS) disease, an autoimmune disease, a fungal infection, a bacterial infection, a cardiovascular disease and AIDS. The central nervous system disease may be epilepsy, rheumatoid or Alzheimer's disease. The autoimmune disease may be rheumatoid arthritis, systemic lupus erythematosus or psoriatic arthritis. The cardiovascular disease may be congestive heart failure or hypertension. Preferably, the disorder is selected from the group consisting of a CNS disease, an autoimmune disease, a fungal infection, a bacterial infection, a cardiovascular disease and AIDS. More preferably, the disorder is epilepsy or rheumatoid arthritis. It is found that the cobalt-polypyridyl complex of the present invention, in particular the cobalt-polypyridyl complex of Formula (IV), is effective in directly binding to the activated form of P-glycoprotein and suppressing the expression and/or functional activity of P-glycoprotein. Therefore, the present invention provides effective P-glycoprotein inhibitor which may be used in a method for treating a disorder associated with an overexpression of ABC transporter protein, in particular an overexpression of P-glycoprotein, in a subject. Further, when the cobalt-polypyridyl complex is administered to a subject in combination with at least one chemotherapeutic compound as described above or a conventional therapeutic agent, the cobalt-polypyridyl complex may be capable of altering at least regional distribution of the chemotherapeutic compound or the conventional therapeutic agent in the subject, via inhibition of the P-glycoprotein.

The method of the present invention may comprise further steps before administering the cobalt-polypyridyl complex, in particular the cobalt-polypyridyl complex of Formula (III), (IV) or (VII), the steps comprises:
- obtaining a sample, in particular cancer cells, from the subject;
- testing said sample for at least one of
   - the expression of at least one ABC-protein, in particular P-glycoprotein;
   - at least one ABC-protein, in particular the P-glycoprotein, functional activity;
- optionally correlating the expression and/or functional activity of the ABC-protein and if conditions are met, administrating the cobalt-polypyridyl complex to said subject; alone or in combination with a further chemotherapeutic compound.

According to the invention is also the cobalt-polypyridyl complex of the present invention, preferably comprising a structure of Formula (III), (IV) or (VII), in particular comprising a structure of Formula (IV), for use as a medicament for the treatment of a disorder associated with an overexpression of the ABC transporter protein in particular an overexpression of P-glycoprotein. In embodiment, the disorder is multidrug-resistant cancer such as P-glycoprotein dependent multidrug-resistant cancer, preferably against at least taxol. The cobalt-polypyridyl complex of the present invention, preferably comprising a structure of Formula (III), (IV) or (VII), in particular comprising a structure of Formula (IV), can be used in an effective amount for treating an animal or a human, in particular mammal, preferably a human.

Another aspect of the invention refers to the use of the cobalt-polypyridyl complex of the present invention, preferably comprising a structure of Formula (III), (IV) or (VII), in particular comprising a structure of Formula (IV), for preparing a medicament for treatment of a disorder associated with an overexpression of an ABC transporter protein, in particular an overexpression of P-glycoprotein. In an embodiment, the disorder is multidrug-resistant cancer such as P-glycoprotein-dependent cancer. In another embodiment, the disorder is selected from the group consisting of a CNS disease, an autoimmune disease, a fungal infection, a bacterial infection, a cardiovascular disease and AIDS. Preferably, the disorder is epilepsy or rheumatoid arthritis and optionally the subject has a drug resistance against a conventional therapeutic agent. The cobalt-polypyridyl complex of the present invention, preferably comprising a structure of Formula (III), (IV) or (VII), in particular comprising a structure of Formula (IV), may be used in combination with at least a further chemotherapeutic compound.

The present invention further provides a method for inhibiting the expression and/or functional activity of an ABC transporter protein in cells. The method comprises the step of contacting a population of cells, in particular cells with an overexpression of the ABC transporter protein with an effective amount of a cobalt-polypyridyl complex. The cobalt-polypyridyl complex comprises a structure of Formula (I):

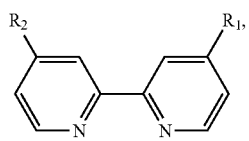

Formula (I)

wherein $R_1$ and $R_2$ are independently selected from hydrogen, a $C_1$-$C_{10}$ alkyl or a $C_1$-$C_{10}$ alkoxy. In particular, the cobalt-polypyridyl complex comprises a structure of Formula (II):

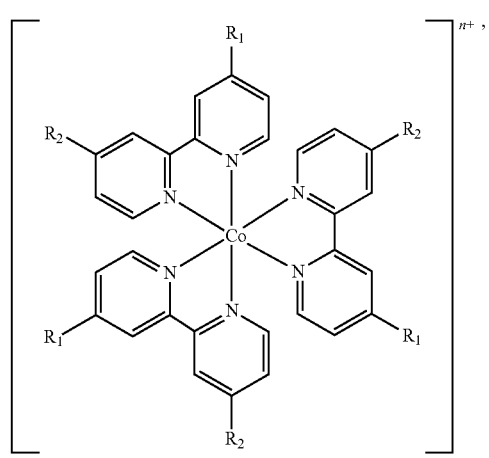

Formula (II)

wherein $R_1$ and $R_2$ are identical and selected from —H, —CH$_3$, —C$_9$H$_{19}$ or —OCH$_3$ and wherein n is 2 or 3.

In preferred embodiments of the present invention, the cobalt-polypyridyl complex used for contacting the cancer cells comprises and in particular essentially consists of a structure of Formula (III), (IV) or (VII) and optionally a counterion:

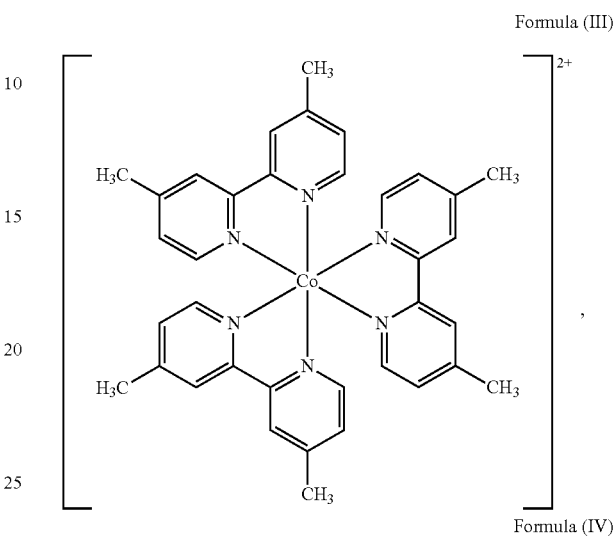

Formula (III)

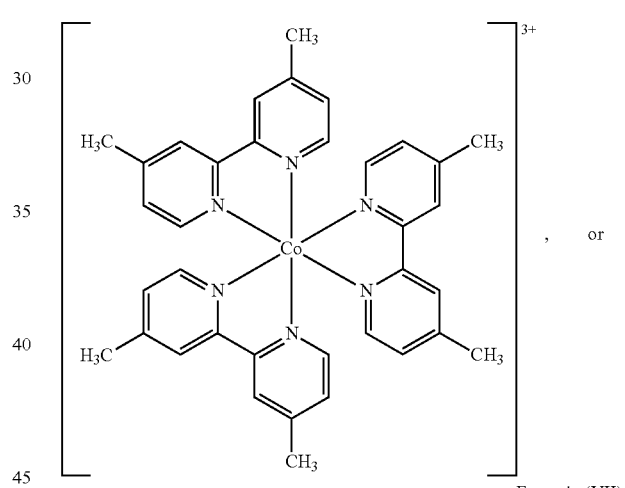

Formula (IV)

, or

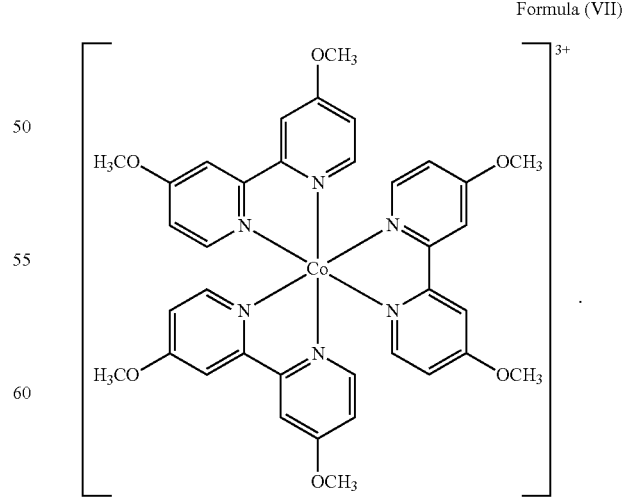

Formula (VII)

The cobalt-polypyridyl complex more preferably comprises a structure of Formula (IV) and optionally a counterion, wherein the cells are contacted with of from about 0.1 µM to about 30 µM of said cobalt-polypyridyl complex. In particular embodiments of the present invention, the cobalt-polypyridyl complex comprises and in particular essentially consists of a structure of Formula (IV) and a counterion, which is a monovalent anion and preferably selected from hexafluorophosphate ($PF_6^-$) or chloride ($Cl^-$) and wherein the cancer cells are contacted with of from about 0.5 µM to about 10 µM of said cobalt-polypyridyl complex.

In an embodiment, the cells are multidrug-resistant cells with an overexpression of the ABC transporter protein, and preferably the multidrug-resistant cells are resistant against at least one of paclitaxel (taxol), doxorubicin, cisplatin, etoposide and staurosporine, in particular against one of taxol or doxorubicin or both of them. In another embodiment, the cells are multidrug-resistant cells against a conventional therapeutic agent used in the disorder selected from the group consisting of a CNS disease, an autoimmune disease, a fungal infection, a bacterial infection, a cardiovascular disease and AIDS.

In a particular embodiment, the cells are multidrug-resistant cancer cells, preferably ABC-protein-dependent, in particular P-glycoprotein-dependent, multidrug-resistant cancer cells. The multidrug-resistant cancer cells are preferably at least resistant against taxol.

The cancer cells are preferably of human origin. The cancer cells are preferably from one of:
an ovarian cancer,
a cervical cancer,
a liver cancer,
a lung cancer,
a breast cancer,
a gastric cancer, or
a colon cancer.

In particular, the cancer cells are selected from the group consisting of breast cancer cells, lung cancer cells and colon cancer cells.

The step of contacting the cancer cells with the cobalt-polypyridyl complex of the present invention, preferably comprising a structure of Formula (III), (IV) or (VII), may be carried out by applying an incubation solution comprising the cobalt-polypyridyl complex to said cells which incubation solution may further comprise suitable excipients such as buffers or a suitable growth medium.

The method may further comprise contacting said cells with a further chemotherapeutic compound; including for example, cisplatin, doxorubicin, taxol, etoposide and staurosporine; before, at the same time with or subsequent to the application of the cobalt-polypyridyl complex of the present invention. In an embodiment, the method may further comprise contacting said cells with a further conventional therapeutic agent used in the treatment of treating a disorder selected from the group consisting of a CNS disease, an autoimmune disease, a fungal infection, a bacterial infection, a cardiovascular disease and AIDS.

The inhibition of P-glycoprotein can be determined with a P-glycoprotein efflux assay by determining the amount of cells in particular multidrug-resistant cancer cells in a sample with marker such as with Rho123 in the presence of the cobalt-polypyridyl complex of the present invention after carrying out the efflux assay compared to a reference control with multidrug-resistant cancer cells in the absence of the cobalt-polypyridyl complex. In particular, the percentage of cells with marker such as Rho123 is at least 20, more preferably at least 30 and in particular at least 40 percentage points increased compared to the reference control by the cobalt-polypyridyl complex of the present invention. Usually, the multidrug-resistant cancer cells are contacted with the cobalt-polypyridyl complex and incubated for at least 12 h, in particular for about 24 h at about 37° C. The reference control is, instead, not incubated with the cobalt-polypyridyl complex. Usually, the marker in particular Rho123 is subsequently added while further incubating at about 37° C. for at least 20 min, preferably for at least 30 min and in particular for about 1 h.

The cobalt-polypyridyl complex of the present invention comprising a cobalt ion in the oxidation state +2 or +3, at least one polypyridyl ligand of Formula (I) and optionally a counterion can be prepared by a method comprising steps of:
(i) providing a mixture of a cobalt salt with a cobalt oxidation state of +2 and the polypyridyl ligand of Formula (I):

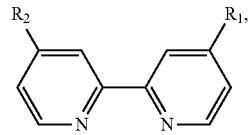

Formula (I)

in a solvent, wherein $R_1$ and $R_2$ are independently selected from hydrogen, a $C_1$-$C_{10}$ alkyl or a $C_1$-$C_{10}$ alkoxy and optionally a further polypyridyl ligand;
(ii) optionally adding a salt comprising the counterion;
(iii) optionally oxidizing the cobalt ion to the oxidation state +3.

The solvent in step (i) preferably comprises an aliphatic alcohol, which means herein an aliphatic hydrocarbon, preferably a branched or straight chain alkane, wherein at least one hydrogen atom of the aliphatic hydrocarbon is substituted with a hydroxyl group, preferably one hydrogen atom is substituted with a hydroxyl group referenced as monohydric aliphatic alcohol. More preferably, the aliphatic alcohol is a monohydric aliphatic alcohol, still more preferably a monohydric alcohol with 1 to 3 carbon atoms, further preferably with 1 to 2 carbon atoms. I.e. the aliphatic alcohol is more preferably selected from methanol, ethanol, propanol or isopropanol or mixtures thereof and further preferably from methanol, ethanol or mixtures thereof. More preferably, the aliphatic alcohol is methanol. The solvent in step (i) most preferably essentially consists of methanol.

Step (i) preferably comprises steps of:
a) preparing a mixture of the cobalt salt with a cobalt oxidation state of +2 and the polypyridyl ligand of Formula (I) in methanol; wherein the molar ratio of the polypyridine ligand of Formula (I) and the cobalt salt is between 2:1 and 4:1, more preferably about 3.3:1;
b) heating the mixture to reflux, preferably under $N_2$ atmosphere for 1 h to 3 h, preferably for about 2 h;
c) cooling the mixture down to a temperature between 20° C. and 30° C., preferably to about 25±2° C.

The cobalt salt is preferably a cobalt chloride or hydrate thereof, more preferably $CoCl_2 \times 6\ H_2O$. The ligand is preferably of Formula (I) with $R_1$ and $R_2$ being identical and selected from —H, —$CH_3$, —$C_9H_{19}$, —$OCH_3$. Preferably, no further polypyridyl ligand is added in step (i).

Step (ii) preferably comprises adding an excess of a salt comprising the counterion, preferably monovalent anions which are in particular selected from $PF_6^-$ or $Cl^-$, for example, adding $NH_4PF_6$. Step (ii) in particular comprises steps of:

a) adding the salt comprising the counterion, in particular in a molar ratio of at least 4:1 compared to the cobalt salt added in step (i);
b) stirring the mixture for 30 min to 90 min, in particular for about 60 min;
c) separating the precipitate by filtration and optional purifying the precipitate and optional drying.

Purification in step c) may be carried out by washing with at least one washing solvent, in particular an aliphatic alcohol and/or an ether, still more preferably a monohydric alcohol with 1 to 3 carbon atoms, further preferably with 1 to 2 carbon atoms and/or an ether, in particular a $C_2$ to $C_6$ dialkyl ether. More preferably, the at least one washing solvent is selected from one or more of methanol, ethanol or diethyl ether. The optional drying may be carried out in vacuum.

Step (iii) preferably comprises steps of:
a) adding an oxidizing agent and a solvent;
b) removing the solvent for obtaining a residue;
c) optionally dissolving the residue in a solvent and adding a salt comprising the counterion;
d) separating the precipitate by filtration and optionally purifying the precipitate and optionally drying.

The oxidizing agent is preferably $NOBF_4$ and used in a molar ratio to the cobalt complex obtained in step (i) of between 0.8:1 and 1.2:1, in particular of about 1:1. The solvent is preferably an organic nitrile, in particular acetonitrile. The mixture in step a) is preferably left at a temperature of between 20° C. and 30° C., preferably about 25±2° C. for about 1 h. The solvent is preferably removed under reduced pressure. The solvent in step c) is preferably an organic nitrile, more preferably acetonitrile. Step c) preferably comprises adding an excess of a salt comprising the counterion, preferably monovalent anions which are in particular selected from $PF_6^-$ or $Cl^-$, for example, adding $NH_4PF_6$, in particular with a molar ratio of at least 4:1 compared to the cobalt complex obtained in step (i). Purifying the precipitate is preferably carried out by recrystallizing the precipitate in a recrystallization solvent comprising a ketone and/or an ether, preferably acetone and/or diethyl ether. Drying may be carried out in vacuum. If desired, a counterion can be readily exchanged with another counterion by any of the methods known to one skilled in the art, including ion exchange chromatography and other ion exchange methods or recrystallization.

In another aspect of the present invention, a method for specifically targeting cancer cells with multidrug-resistance is provided, in particular ABC-protein-dependent multidrug-resistant cancer cells such as P-glycoprotein dependent multidrug-resistant cancer cells. Said method comprises the step of contacting a population of cancer cells with multidrug-resistance such as in a sample from a subject or in a subject with the cobalt-polypyridyl complex described above. The multidrug-resistant cancer cells are in particular ABC-protein-dependent, most preferably P-glycoprotein-dependent.

The multidrug-resistant cancer cells can be of any origin, in particular human origin. In particular, the multidrug-resistant cancer cells are from a multidrug-resistant:
ovarian cancer,
cervical cancer,
liver cancer,
lung cancer,
breast cancer
gastric cancer, or
colon cancer.

In preferred embodiments of the present invention, the multidrug-resistant cancer cells are resistant against at least one of paclitaxel (taxol), doxorubicin, cisplatin, etoposide and staurosporine, in particular against at least taxol.

In especially preferred embodiments of the present invention, the cobalt-polypyridyl complex used for contacting the multidrug-resistant cancer cells comprises and in particular essentially consists of a structure of Formula (III), (IV) or (VII) and optionally a counterion:

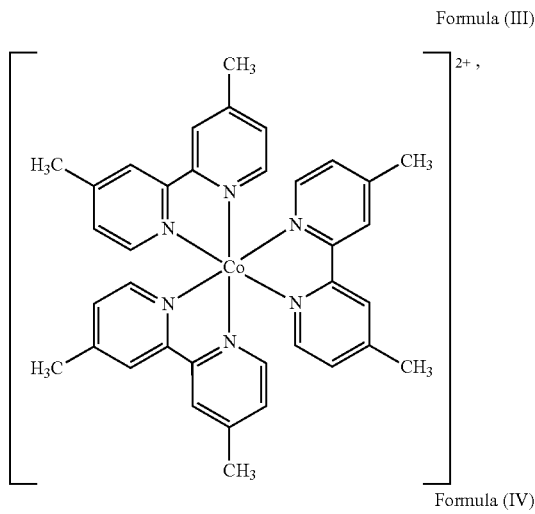

Formula (III)

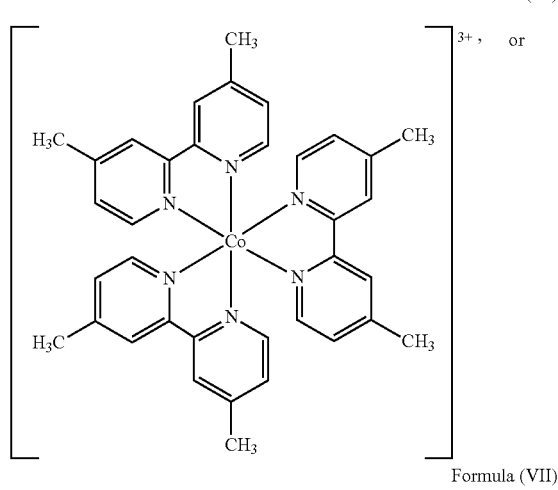

Formula (IV)

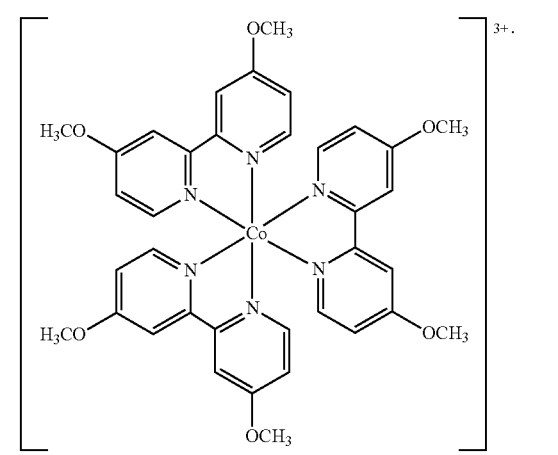

Formula (VII)

The cobalt-polypyridyl complex more preferably comprises a structure of Formula (IV) and optionally a counterion, wherein the multidrug-resistant cancer cells are contacted with of from about 0.5 µM to about 10 µM of said cobalt-polypyridyl complex. In particular embodiments of the present invention, the cobalt-polypyridyl complex comprises and in particular essentially consists of a structure of Formula (IV) and a counterion, which is a monovalent anion and preferably selected from hexafluorophosphate ($PF_6^-$) or chloride ($Cl^-$).

The step of contacting the cancer cells with the cobalt-polypyridyl complex of the present invention, in particular comprising a structure of Formula (III), (IV) or (VII), may be carried out by applying an incubation solution comprising the cobalt-polypyridyl complex to said cells which incubation solution may further comprise suitable excipients such as buffers or a suitable growth medium.

The method may further comprise contacting said cells with a further chemotherapeutic compound; including for example, cisplatin, doxorubicin, taxol, etoposide and staurosporine; before, at the same time with or subsequent to the application of the cobalt-polypyridyl complex of the present invention.

Further in accordance with the present invention is a composition comprising the cobalt-polypyridyl complex and an excipient such as selected from a pharmaceutically acceptable carrier, salt, buffer, water, or a combination thereof. More preferably, the composition is a pharmaceutical composition comprising an effective dose of the cobalt-polypyridyl complex and at least one pharmaceutically tolerable excipient such as selected from at least one of a diluent, a filler, a binder, a disintegrant, a lubricant, a coloring agent, a surfactant or a preservative.

The skilled person is able to select suitable pharmaceutically tolerable excipients depending on the form of the pharmaceutical composition and is aware of methods for manufacturing pharmaceutical compositions as well as able to select a suitable method for preparing the pharmaceutical composition depending on the kind of pharmaceutically tolerable excipients and the form of the pharmaceutical composition. The pharmaceutical composition according to the invention can be present in solid, semisolid or liquid form to be administered by an oral, rectal, topical, parenteral or transdermal or inhalative route to a subject, preferably a human.

Further in accordance with the present invention is a kit comprising an effective dose of:
(i) a cobalt-polypyridyl complex as described above;
(ii) at least one chemotherapeutic compound selected from the group consisting of a topoisomerase-II inhibitor, an anthracycline, a coordination complex of platinum, a taxane, a protein kinase inhibitor, a vinca alkaloid or derivative thereof, a topoisomerase-I inhibitor and a nucleotide analog or precursor analog.

The kit may comprise excipients, in particular pharmaceutically tolerable excipients, such as a carrier, salt, buffer, water, or a combination thereof. The skilled person is able to select suitable excipients. Still further, the kit may comprise at least one container.

Preferably, the cobalt-polypyridyl complex in the pharmaceutical composition or the kit comprises and in particular essentially consists of a structure of Formula (III), (IV) or (VII) and optionally a counterion:

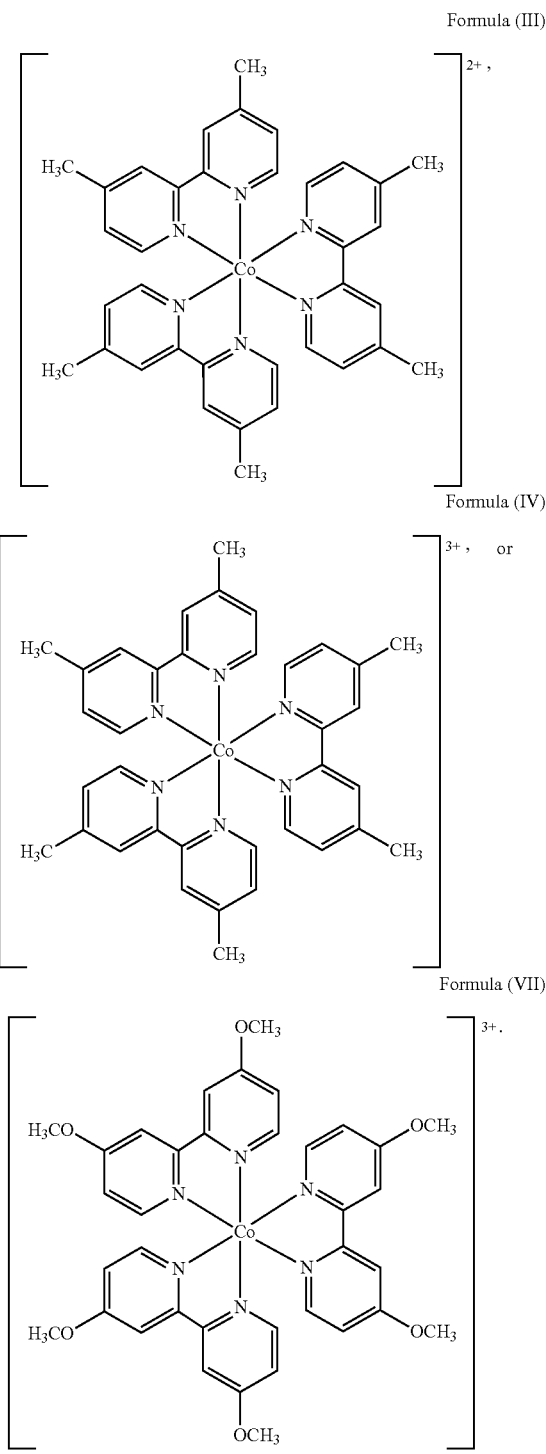

The cobalt-polypyridyl complex more preferably comprises a structure of Formula (IV) and optionally a counterion. In particular embodiments of the present invention, the cobalt-polypyridyl complex comprises and in particular essentially consists of a structure of Formula (IV) and a counterion, which is a monovalent anion and preferably selected from hexafluorophosphate ($PF_6^-$) or chloride ($Cl^-$).

Still another aspect of the present invention concerns the use of the pharmaceutical composition or the kit described above for suppressing the growth of cancer cells, in particular multidrug-resistant cancer cells, more preferably for inhibiting P-glycoprotein of the cancer cells.

EXAMPLES

Example 1

Preparation of Cobalt-Polypyridyl Complexes of the Present Invention

Cobalt-polypyridyl complexes of Formula (V) and (VI) with a counterion were synthesized according to the method below. Other cobalt-polypyridyl complexes were prepared by the modification of the reported procedure.

Preparation of $[Co^{II}(N^{\wedge}N)_3](PF_6)_2$ (Cobalt-Polypyridyl Complex of Formula (V) with $PF_6^-$ as Counterion)

A mixture of $CoCl_2.6H_2O$ (4 mmol) and 2,2'-bipyridine (13.2 mmol) in methanol (100 mL) was heated to reflux under $N_2$ for 2 h. After cooling down to room temperature, $NH_4PF_6$ (20 mmol) was added to the reaction mixture and the reaction mixture was stirred for another 1 h. The precipitate was filtrated and washed with methanol and then diethyl ether.

Preparation of $[Co^{III}(N^{\wedge}N)_3](PF_6)_3$ (Cobalt-Polypyridyl Complex of Formula (VI) with $PF_6^-$ as Counterion)

Oxidation of $[Co^{II}(N^{\wedge}N)_3](PF6)_2$ (2 mmol) was carried out by the treatment of $NOBF_4$ (2 mmol) in acetonitrile (40 mL) at room temperature for 1 h. After removing the solvent under reduced pressure, the residue was dissolved in acetonitrile (10 mL) and $NH_4PF_6$ (10 mmol) was added. The precipitate was collected by filtration and the solid was purified by recrystallization of acetone/diethyl ether to afford the crystal form of the desired product.

$[Co^{II}(4,4'-Me_2-bpy)_3](PF_6)_2$ (Cobalt-Polypyridyl Complex of Formula (III) with $PF_6^-$ as Counterion)

This complex has been obtained as yellow solid in 95% yield. Positive-ion ESI-MS ion cluster at m/z (%): 756.20 $[M-PF_6^-]^+$. IR (KBr) v/cm$^{-1}$: 843 ($PF_6^-$). Anal. Calcd for $CoH_{36}H_{36}N_6F_2P_{12}.H_2O$ (%): C, 47.02; H, 4.17; N, 9.14. Found: C, 46.88; H, 4.14; N, 9.13.

$[Co^{III}(4,4'-Me_2-bpy)_3](PF_6)_3$ (Cobalt-Polypyridyl Complex of Formula (IV) with $PF_6^-$ as Counterion)

This complex has been obtained as yellow crystals in 88% yield (through two steps). $^1$H NMR (300 MHz, DMSO-d$_6$, 298K, TMS)/ppm: δ 8.91 (s, 2H, H3 of bpy), 7.61 (d, 2H, J=4.8 Hz, H6 of bpy), 7.27 (d, 2H, J=4.8 Hz, H5 of bpy), 2.63 (s, 6H, CH$_3$). $^{13}$C NMR (75 MHz, DMSO-d$_6$, 298K, TMS)/ppm: δ 156.7, 155.2, 150.4, 132.2, 127.9, 21.5. IR (KBr) v/cm$^{-1}$: 853 ($PF_6^-$). Positive-ion ESI-MS ion cluster at m/z 901.2 $[M-PF_6^-]^+$, 305.6 $[M-2\times PF_6^-]^{2+}$, 302.7 $[M-3\times PF_6^-]^{3+}$. Anal. Calcd for $CoH_{36}H_{36}N_6F_3P_{18}.MeOH$ (%): C, 41.20; H, 3.74; N, 7.79. Found: C, 41.09; H, 4.09; N, 7.82.

$[Co^{III}(4,4'-OMe)_2-bpy)_3](PF_6)_3$ (Cobalt-Polypyridyl Complex of Formula (VII) with $PF_6^-$ as Counterion)

This complex has been obtained as orange crystals in 87% yield (through two steps). $^1$H NMR (300 MHz, DMSO-d$_6$, 298K, TMS)/ppm: δ 8.68 (s, 2H, H3 of bpy), 7.32 (d, 2H, J=5.1 Hz, H6 of bpy), 7.21 (d, 2H, J=5.1 Hz, H5 of bpy), 4.09 (s, 6H, OCH$_3$). $^{13}$C NMR (75 MHz, DMSO-d$_6$, 298K, TMS)/ppm: δ 170.6, 156.8, 151.6, 117.4, 114.1, 58.2. IR (KBr) v/cm$^{-1}$: 845 ($PF_6^-$). Positive-ion ESI-MS ion cluster at m/z 997.1 $[M-PF_6^-]^+$, 426.1 $[M-2\times PF_6^-]^+$, 235.7 $[M-3\times PF_6^-]^+$. Anal. Calcd for $CoH_{36}H_{36}O_6N_6F_3P_{18}.2H_2O$ (%): C, 36.39; H, 3.42; N, 7.13. Found: C, 36.66; H, 3.50; N, 7.24.

$[Co^{III}(4,4'-(C_9H_{19})_2-bpy)_3](PF_6)_3$ (Cobalt-Polypyridyl Complex of Formula (VIII) with $PF_6^-$ as Counterion)

This complex has been obtained as yellow crystals in 85% yield (through two steps). $^1$H NMR (300 MHz, DMSO-d$_6$, 298K, TMS)/ppm: δ 8.95 (s, 2H, H3 of bpy), 7.64 (d, 2H, J=4.8 Hz, H6 of bpy), 7.24 (d, 2H, J=4.8 Hz, H5 of bpy), 2.88 (t, 4H, J=5.7 Hz, CH$_2$), 1.71-1.67 (m, 4H, CH$_2$), 1.31-1.20 (m, 24H, CH$_2$), 0.87 (t, 6H, J=5.1 Hz, CH$_3$). $^{13}$C NMR (75 MHz, DMSO-d$_6$, 298K, TMS)/ppm: δ 160.6, 155.5, 150.8, 131.3, 127.2, 35.0, 31.7, 29.7, 29.4, 29.2, 29.1, 22.6, 14.4. IR (KBr) v/cm$^{-1}$: 835 ($PF_6^-$). Positive-ion ESI-MS ion cluster at m/z 1574.9 $[M-PF_6^-]^+$, 714.5 $[M-2\times PF_6^-]^{2+}$, 428.0 $[M-3\times PF_6^-]^{3+}$. Anal. Calcd for $CoH_{84}H_{132}N_6F_3P_{18}.CH_3CH_2OCH_2CH_3$ (%): C, 58.92; H, 7.98; N, 4.68. Found: C, 59.03; H, 7.93; N, 4.65.

Example 2

Cytotoxicity Assays

The prepared cobalt-polypyridyl complex of Formula (IV) (with $PF_6^-$ as counterion) was dissolved in DMSO at a final concentration of 50 mmol/L and stored at −20° C. before use. Cytotoxicity was assessed by using the 3-(4,5-dimethylthiazol-2-yl)-2,5-diphenyltetrazolium bromide (MTT) (5.0 mg/ml) assay as previously described (Wong, V. K. et al., Cell Death Dis, 2013, 4, e720). Briefly, 4×10$^3$ cells per well were seeded in 96-well plates before drug treatments. After overnight culture, the cells were then exposed to different concentrations of selected compounds (0.039-100 μmol/L) for 72 h. Cells without drug treatment were used as control. Subsequently, MTT (10 μL) solution was added to each well and incubated at 37° C. for 4 h followed by the addition of 100 μL solubilization buffer (10% SDS in 0.01 mol/L HCl) and overnight incubation. $A_{570}$ nm was then determined in each well on the next day. The percentage of cell viability was calculated using the following formula: Cell viability (%)=$A_{treated}/A_{control}\times100$. Data were obtained from three independent experiments. Cells include MCF-7 (breast cancer) taxol-sensitive and -resistant pairs, HCT-8 (colon cancer) taxol-sensitive and -resistant pair, A549 (lung cancer) taxol-sensitive and -resistant pairs.

Figure 1B:
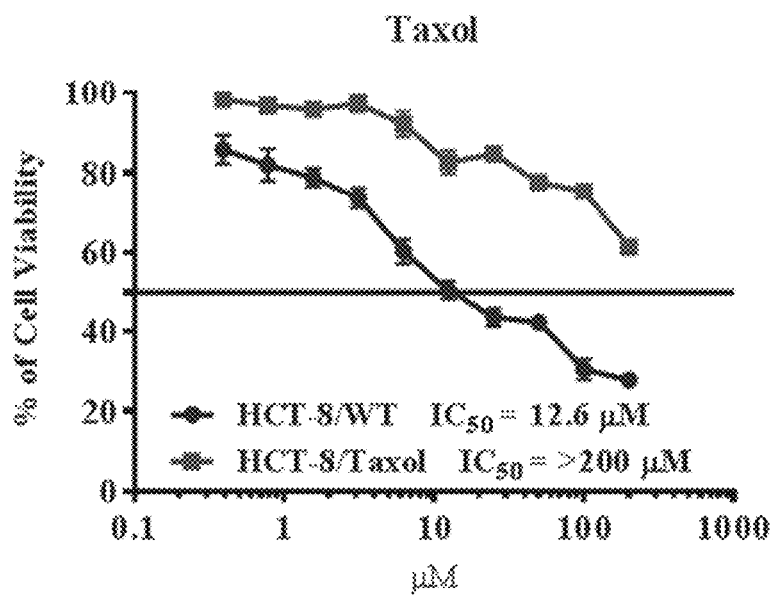
FIG. 1B is a diagram showing the percentage of cell viability of taxol-resistant HCT-8 colon cancer cells after the treatment with the cobalt-polypyridyl complex of Formula (IV) with $PF_6^-$ as counterion and in the control group.
Figure 1C:
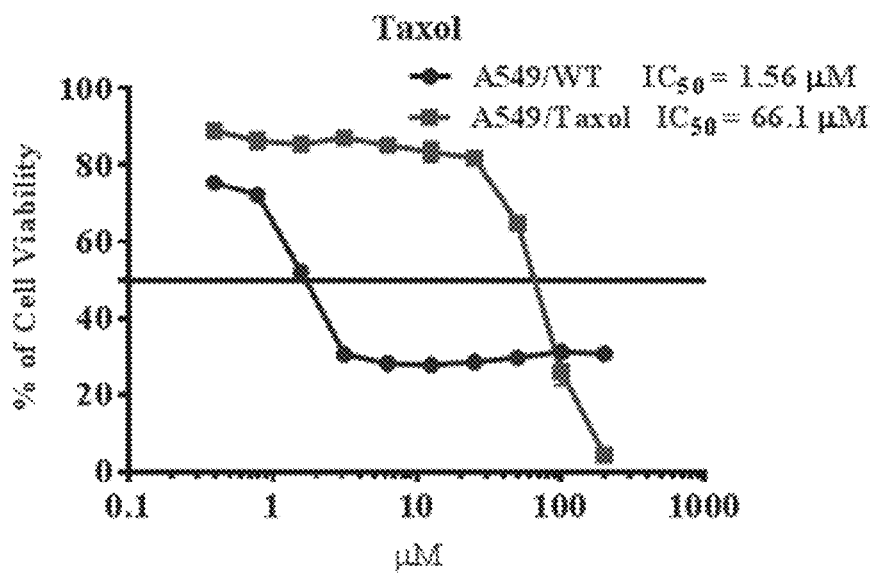
FIG. 1C is a diagram showing the percentage of cell viability of taxol-resistant A549 lung cancer cells after the treatment with the cobalt-polypyridyl complex of Formula (IV) with $PF_6^-$ as counterion and in the control group.

As shown in FIG. 1A, taxol-resistant MCF-7 breast cancer cells displayed drug-resistant effect toward taxol from 12.2 μM increased to 55 μM. In addition, with reference to FIG. 1B, taxol-resistant HCT-8 colon cancer cells displayed drug resistant toward taxol from 12.6 μM increased up to 200 μM. Besides, with reference to FIG. 1C, taxol-resistant A549 lung cancer cells also displayed drug resistant toward taxol from 1.56 μM increased to 66.1 μM. These results demonstrate the drug-resistant phenotypes of these cancer cells toward the chemotherapeutic agent, taxol.

Example 3

Protein Extraction and Western Blotting Detection of P-Glycoprotein

After treating the cancer cells with the polypyridyl complexes, adherent and floating cells were lysed with RIPA lysis buffer. Protein concentrations were determined using the Bio-Rad protein assay (Bio-Rad Laboratories, Inc., Hercules, Calif., USA). The cell lysates of samples were subjected to electrophoresis on SDS polyacrylamide gels and transferred to Hybond enhanced chemiluminescence nitrocellulose membranes (Amersham Biosciences, Piscataway, N.J.), which were then blocked with 5% non-fat dry milk protein for 1 h. Membranes were then incubated with the ABCB5 or actin primary antibodies overnight at 4° C. The binding of the antibody was visualized by peroxidase-coupled secondary antibody using the ECL Western Blotting Detection Reagents (Invitrogen, Paisley, Scotland, UK). Band intensities were quantified by using the software ImageJ (NIH, Bethesda, Md., USA).

Figure 2:
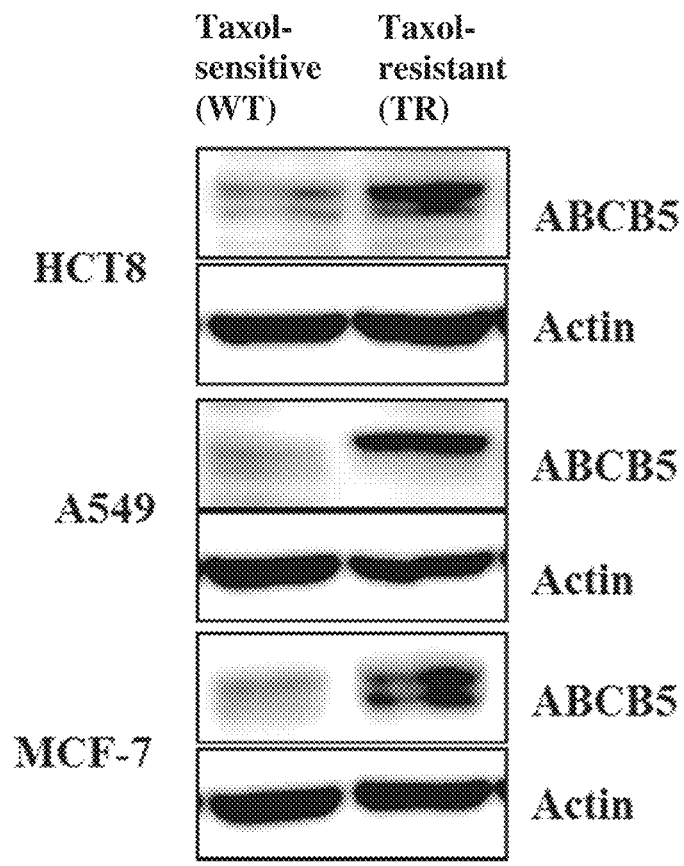
FIG. 2 is a Western Blot showing the expression of P-glycoprotein (ABCB5) in the taxol-sensitive (WT) group and taxol-resistant group of HCT-8 colon cancer, A549 lung cancer and MCF-7 breast cancer, wherein β-actin was used as control.

As shown in FIG. 2, the P-glycoprotein, ABCB5 was detected in both taxol-sensitive and taxol-resistant HCT-8 colon cancer, A549 lung cancer and MCF-7 breast cancer cells. Of noted, the P-glycoprotein, ABCB5 was strongly expressed in taxol-resistant (TR) cells compared to their sensitive counterpart (WT). Therefore, the taxol-resistance or drug-resistance in these cancer cells is caused by the increased expression of P-glycoprotein, ABCB5.

Example 4

Effects of Cobalt-Polypyridyl Complex of Formula (IV) in MCF-7 Taxol-Resistant Breast Cancer Cells A Rho123 efflux assay has been carried out. MCF-7 taxol-resistant breast cancer cells were seeded in a 6 well-plate at a final concentration of $2\times10^5$ cells per well and cultured for 24 h at 37° C. in an atmosphere containing 5% $CO_2$. At confluence, 3 mL fresh media with or without 0.5 µM, 1 µM, 2 µM, 5 µM and 10 µM cobalt-polypyridyl complex of Formula (IV), or 10 µM verapamil (a known P-glycoprotein inhibitor) was added and incubated further at 37° C. for 24 h. Subsequently, 5 mg/mL Rho123 was added to each well and the wells were incubated for another 1 h at 37° C. At the end of the incubation, the accumulation of Rho123 was stopped by washing the cells five times with ice-cold PBS. After cell centrifugation, cell pellets were resuspended in 400 µL PBS. Intracellular fluorescence was measured using a flow cytometer at an excitation wavelength of 488 nm and emission wavelength of 525 nm. All data acquisition and analyses were performed with CellQuest (BD Biosciences, San Jose, Calif., USA) in triplicate in three independent experiments, and the results were shown as the mean of fluorescence intensity.

Figure 3A:
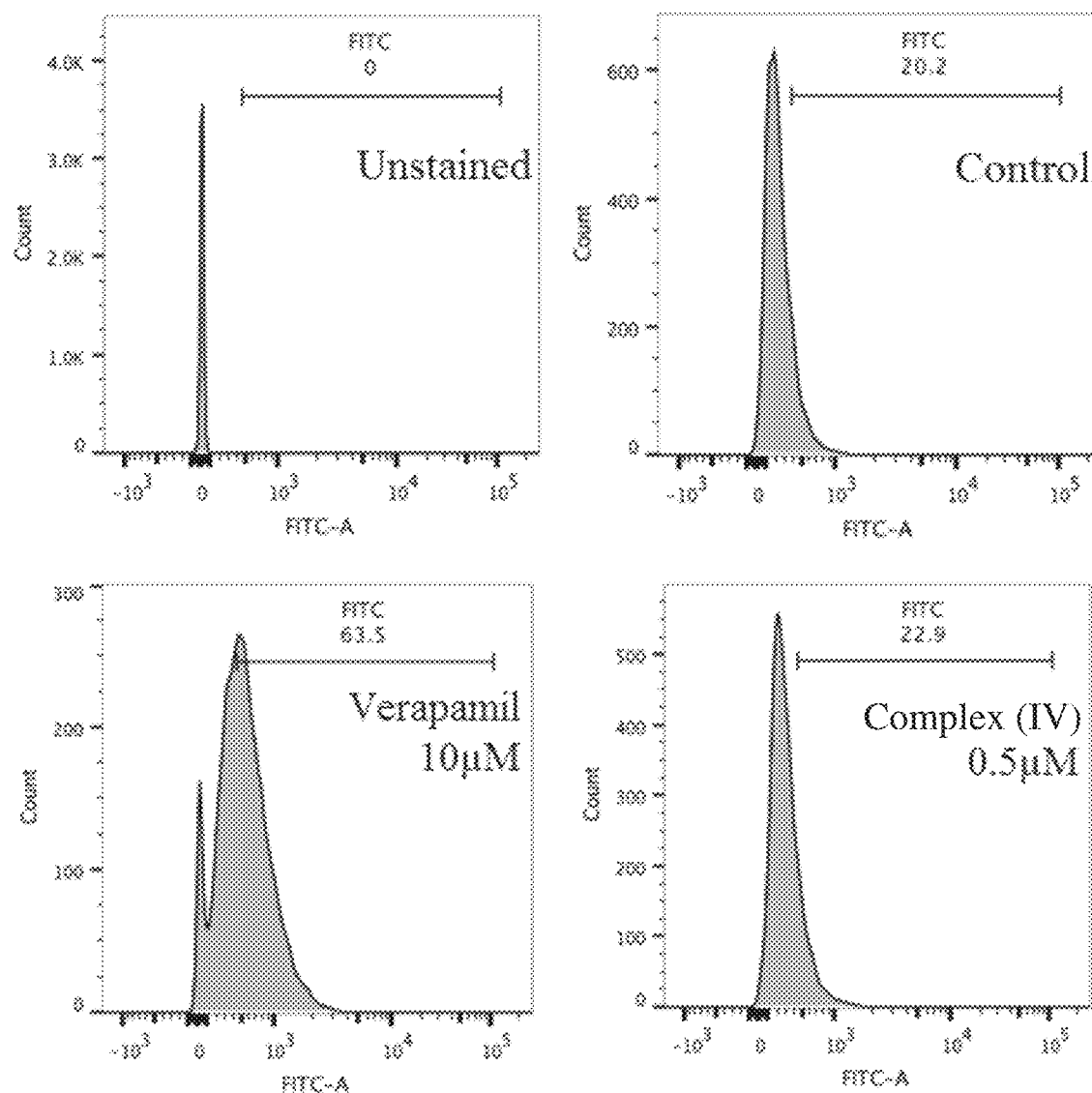
FIGS. 3A and 3B show the effects of the cobalt-polypyridyl complex of Formula (IV) on taxol-resistant MCF-7 breast cancer cells as determined by a Rho123 efflux assay in combination with flow cytometry. The cancer cells were treated with Rho123 dye in the presence of a P-glycoprotein inhibitor verapamil (10 μM) or the complex of Formula (IV) with 0.5 μM, 1 μM, 2 μM, 5 μM or 10 μM compared to an unstained group and a control group with cells treated with Rho123 dye only.
Figure 3B:
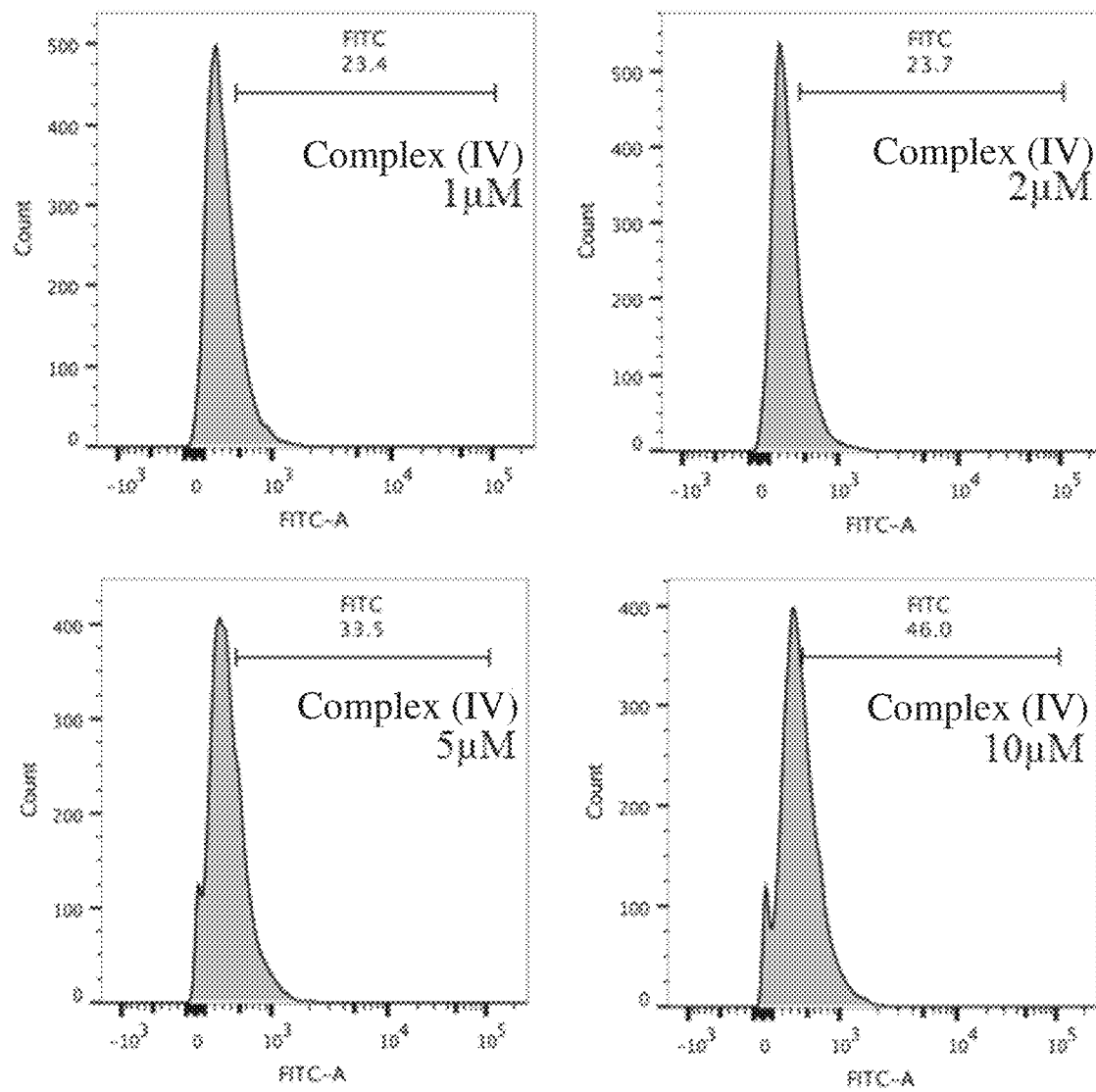
Figure 3C:
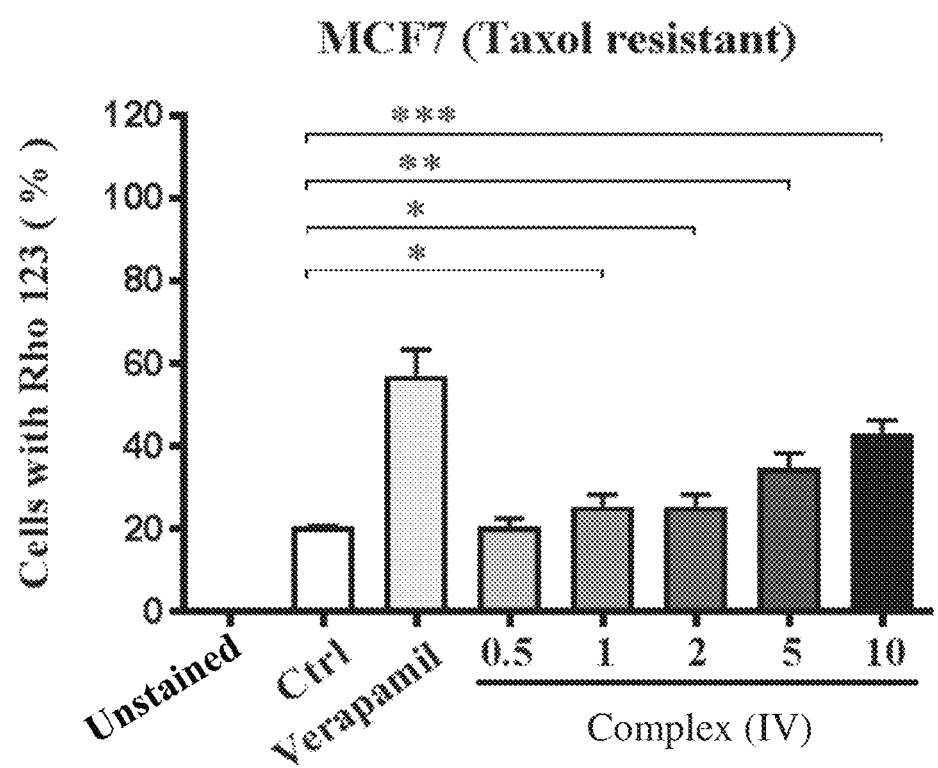
FIG. 3C is a bar chart showing the percentage of taxol-resistant MCF-7 breast cancer cells dyed with Rho123 upon the treatment with verapamil or cobalt-polypyridyl complex of Formula (IV), compared to the unstained group and the control group.

As shown in FIG. 3A to FIG. 3C, Rho123 dye staining in taxol-resistant breast cancer cells, i.e. the control group, only yielded 20% of cell population with fluorescence signal, suggesting that P-glycoprotein in these taxol-resistant cancer cells effectively pumped out the Rho123 dye from the cells. However, addition of the P-glycoprotein inhibitor verapamil significantly suppressed the P-glycoprotein activity, leading to a marked increase of Rho123 fluorescence signal in cells. Meanwhile, the cobalt-polypyridyl complex of Formula (IV) dose-dependently inhibited the P-glycoprotein activity, thereby increased the Rho123 accumulation in taxol-resistant cancer cells. Collectively, these results confirm that the cobalt-polypyridyl complex of Formula (IV) is a potent P-glycoprotein inhibitor at least as effective as verapamil, as it advantageously inhibits P-glycoprotein functional activity in MCF-7 taxol-resistant breast cancer cells.

Example 5

Effects of Cobalt-Polypyridyl Complex of Formula (IV) in HCT-8 Taxol-Resistant Colon Cancer Cells A Rho123 efflux assay has been carried out. HCT-8 taxol-resistant colon cancer cells were seeded in a 6 well-plate at a final concentration of $2\times10^5$ cells per well and cultured for 24 h at 37° C. in an atmosphere containing 5% $CO_2$. At confluence, 3 mL fresh media with or without 0.5 µM, 1 µM, 2 µM, 5 µM and 10 µM cobalt-polypyridyl complex of Formula (IV), or 10 µM verapamil was added and incubated further at 37° C. for 24 h. Subsequently, 5 mg/mL Rho123 was added to each well and the wells were incubated for another 1 h at 37° C. At the end of the incubation, the accumulation of Rho123 was stopped by washing the cells five times with ice-cold PBS. After cell centrifugation, cell pellets were resuspended in 400 µL PBS. Intracellular fluorescence was measured using a flow cytometer at an excitation wavelength of 488 nm and emission wavelength of 525 nm. All data acquisition and analyses were performed with CellQuest (BD Biosciences, San Jose, Calif., USA) in triplicate in three independent experiments, and the results were shown as the mean of fluorescence intensity.

Figure 4A:
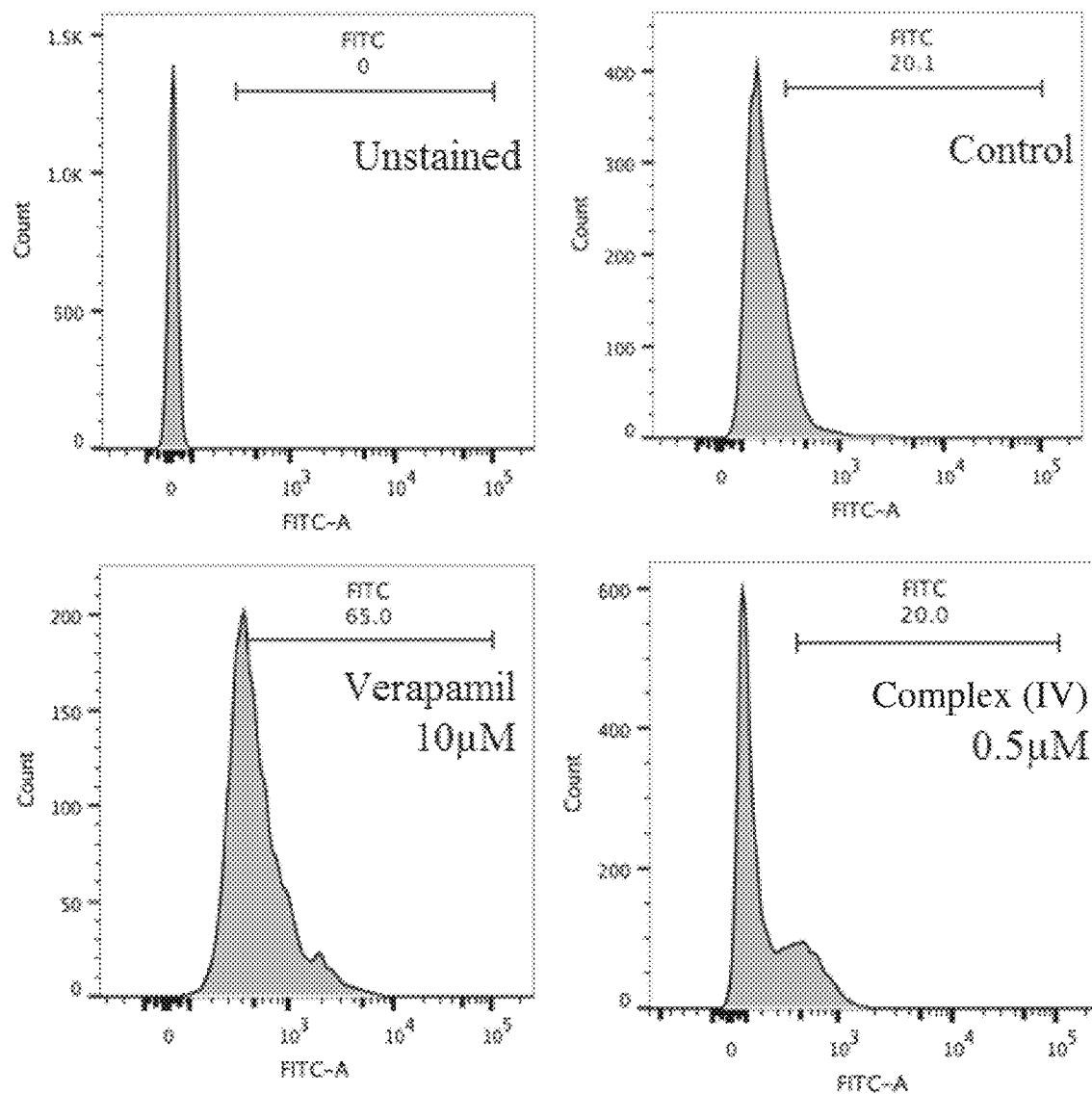
FIGS. 4A and 4B show the effects of the cobalt-polypyridyl complex of Formula (IV) on taxol-resistant HCT-8 colon cancer cells as determined by a Rho123 efflux assay in combination with flow cytometry. The cancer cells were treated with Rho123 dye in the presence of a P-glycoprotein inhibitor verapamil (10 μM) or the complex of Formula (IV) with 0.5 μM, 1 μM, 2 μM, 5 μM or 10 μM compared to an unstained group and a control group with cells treated with Rho123 dye only.
Figure 4B:
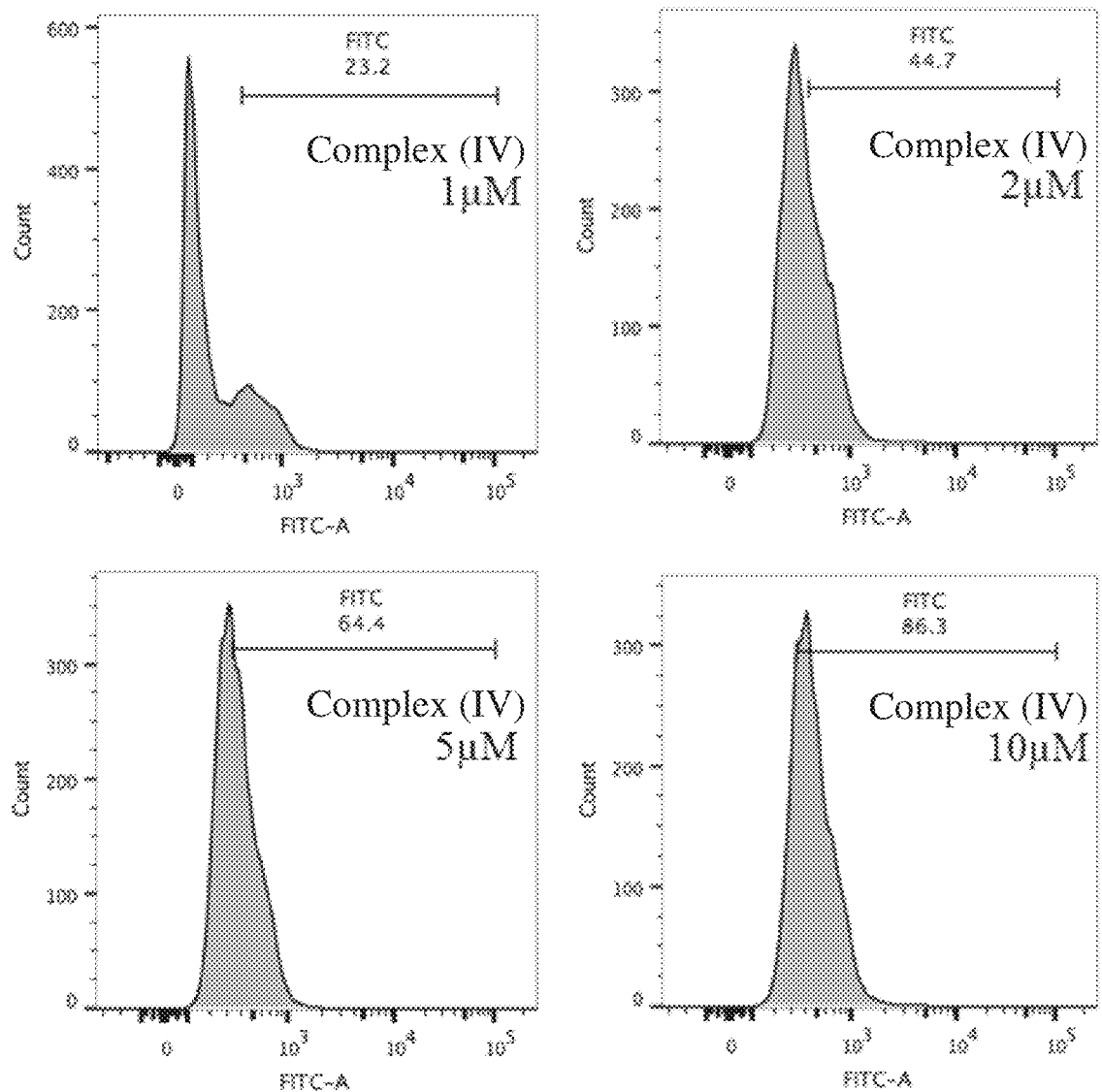
Figure 4C:
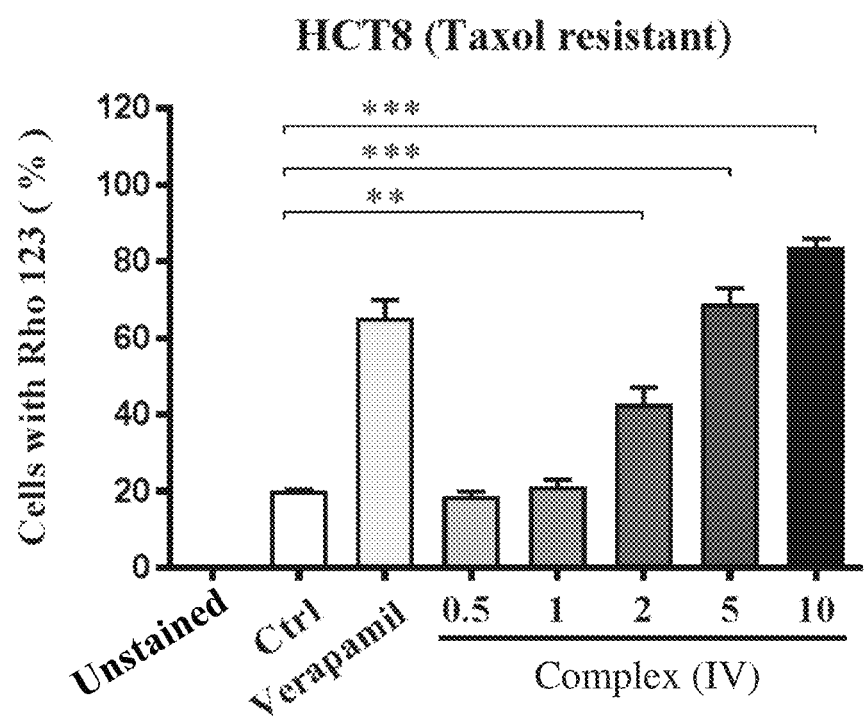
FIG. 4C is a bar chart showing the percentage of taxol-resistant HCT-8 colon cancer cells dyed with Rho123 upon the treatment with verapamil or cobalt-polypyridyl complex of Formula (IV), compared to the unstained group and the control group.

As shown in FIG. 4A to FIG. 4C, Rho123 dye staining in taxol-resistant colon cancer cells, i.e. the control group, only yielded 20% of cell population with fluorescence signal, suggesting that P-glycoprotein in these taxol-resistant cancer cells effectively pumped out the Rho123 dye from the cells. However, addition of the P-glycoprotein inhibitor verapamil significantly suppressed the P-glycoprotein activity, leading to a marked increase of Rho123 fluorescence signal in cells. Meanwhile, cobalt-polypyridyl complex of Formula (IV) dose-dependently inhibited the P-glycoprotein activity, thereby increased the Rho123 accumulation in taxol-resistant cancer cells. Collectively, these results confirm that cobalt-polypyridyl complex of Formula (IV) is a potent P-glycoprotein inhibitor and is at least as effective as verapamil. The cobalt-polypyridyl complex of Formula (IV) advantageously inhibits P-glycoprotein functional activity in HCT-8 taxol-resistant colon cancer cells.

Example 6

Effects of Cobalt-Polypyridyl Complex of Formula (IV) in A549 Taxol-Resistant Lung Cancer Cells A Rho123 efflux assay has been carried out. A549 taxol-resistant lung cancer cells were seeded in a 6 well-plate at a final concentration of $2\times10^5$ cells per well and cultured for 24 h at 37° C. in an atmosphere containing 5% $CO_2$. At confluence, 3 mL fresh media with or without 0.5 µM, 1 µM, 2 µM, 5 µM and 10 µM cobalt-polypyridyl complex of Formula (IV), or 10 µM verapamil was added and incubated further at 37° C. for 24 h. Subsequently, 5 mg/mL Rho123 was added to each well and the wells were incubated for another 1 h at 37° C. At the end of the incubation, the accumulation of Rho123 was stopped by washing the cells five times with ice-cold PBS. After cell centrifugation, cell pellets were resuspended in 400 µL PBS. Intracellular fluorescence was measured using a flow cytometer at an excitation wavelength of 488 nm and emission wavelength of 525 nm. All data acquisition and analyses were performed with CellQuest (BD Biosciences, San Jose, Calif., USA) in triplicate in three independent experiments, and the results were shown as the mean of fluorescence intensity.

Figure 5A:
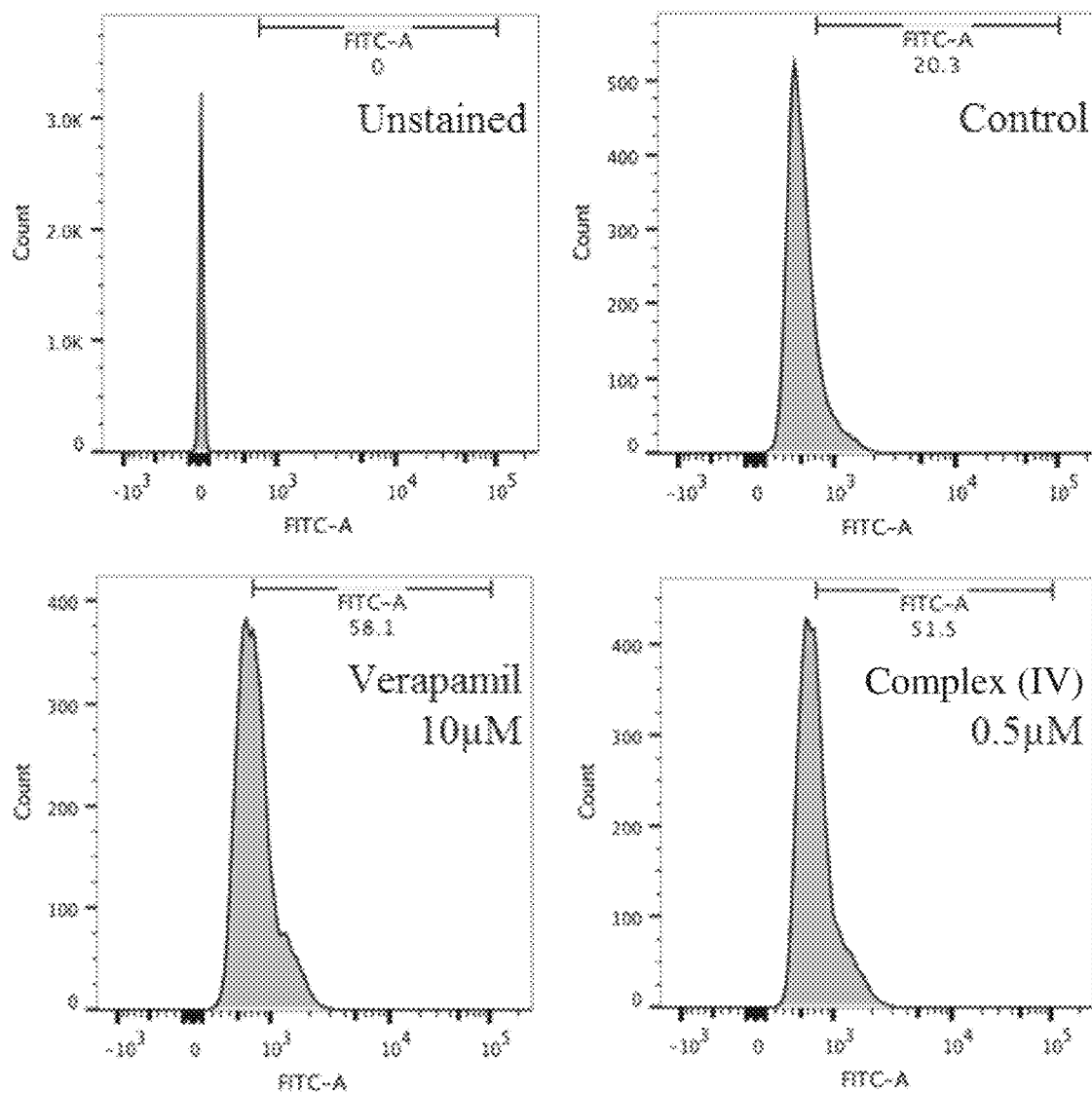
FIGS. 5A and 5B show the effects of the cobalt-polypyridyl complex of Formula (IV) on taxol-resistant A549 lung cancer cells as determined by a Rho123 efflux assay in combination with flow cytometry. The cancer cells were treated with Rho123 dye in the presence of a P-glycoprotein inhibitor verapamil (10 μM) or the complex of Formula (IV) with 0.5 μM, 1 μM, 2 μM, 5 μM or 10 μM compared to an unstained group and a control group with cells treated with Rho123 dye only.
Figure 5B:
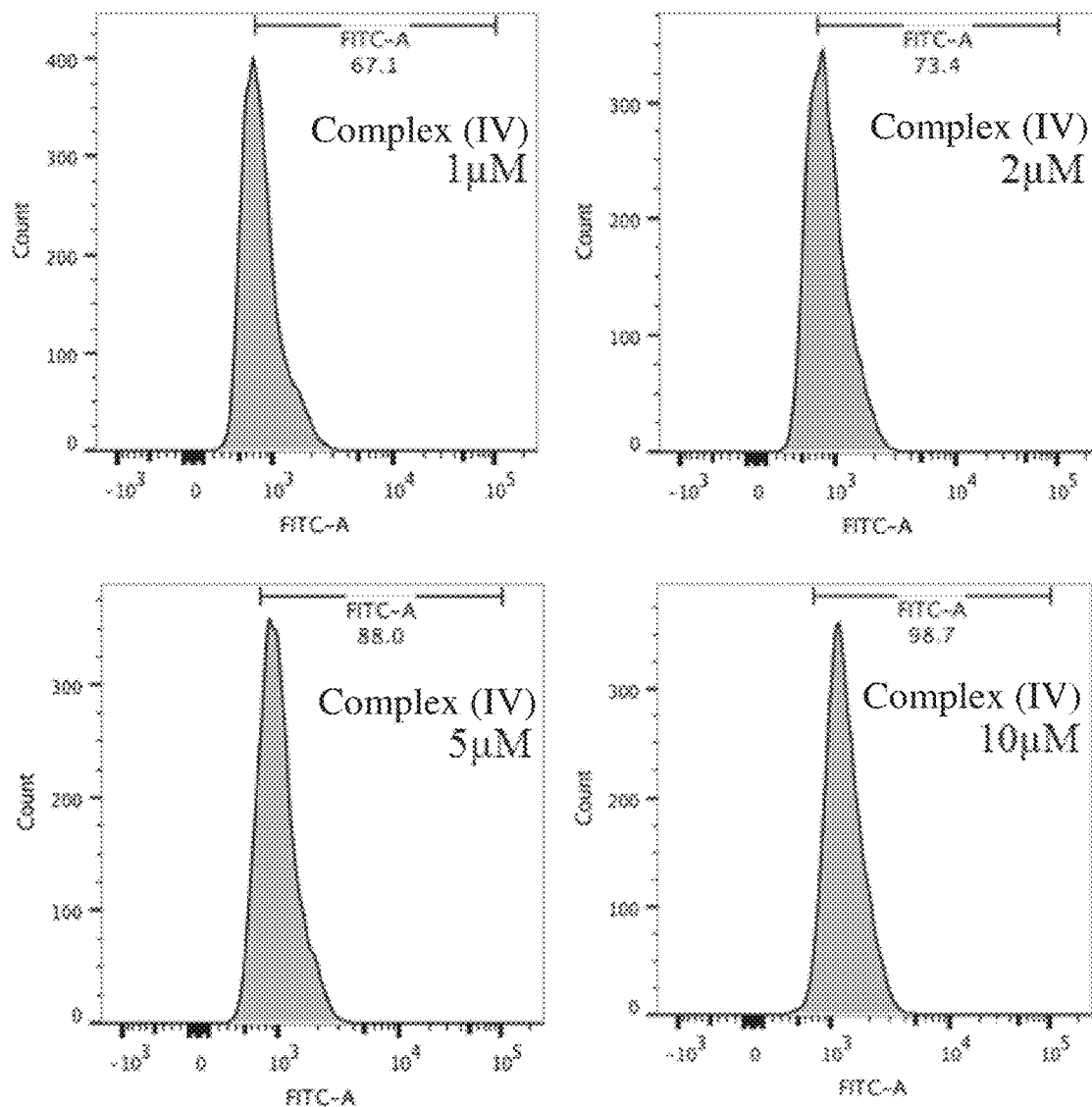
Figure 5C:
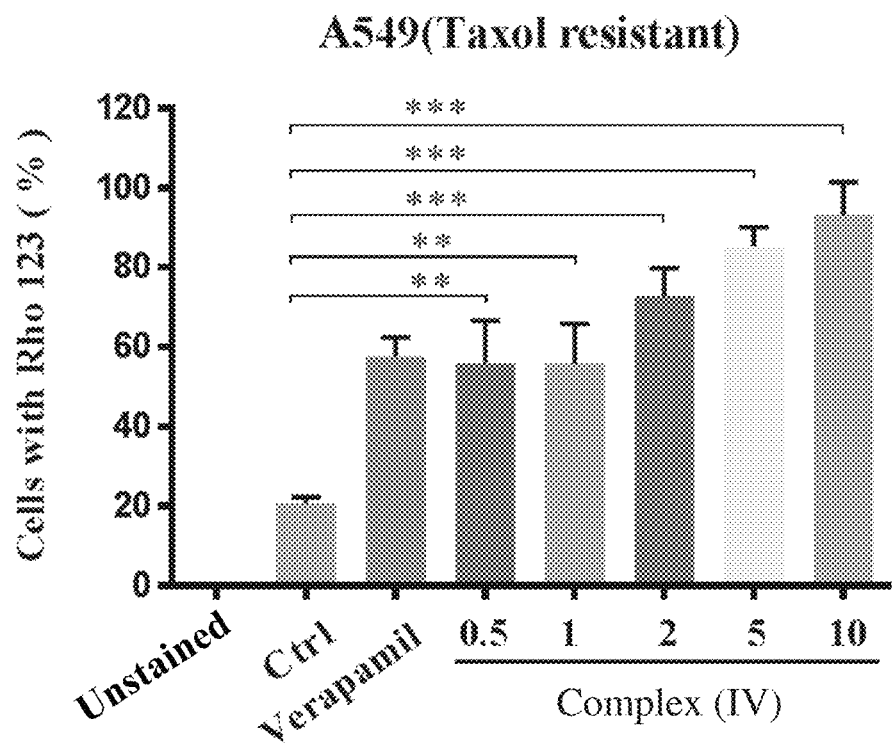
FIG. 5C is a bar chart showing the percentage of taxol-resistant A549 lung cancer cells dyed with Rho123 upon the treatment with verapamil or cobalt-polypyridyl complex of Formula (IV), compared to the unstained group and the control group.

As shown in FIG. 5A to FIG. 5C, Rho123 dye staining in taxol-resistant lung cancer cells, i.e. a control group, only yielded 20% of cell population with fluorescence signal, suggesting that P-glycoprotein in these taxol-resistant cancer cells effectively pumped out the Rho123 dye from the cells. However, addition of the P-glycoprotein inhibitor verapamil significantly suppressed the P-glycoprotein activity, leading to a marked increase of Rho123 fluorescence signal in cells. Meanwhile, cobalt-polypyridyl complex of Formula (IV) dose-dependently inhibited the P-glycoprotein activity, thereby increased the Rho123 accumulation in taxol-resistant cancer cells. Collectively, these results confirm that cobalt-polypyridyl complex of Formula (IV) is a potent P-glycoprotein inhibitor and is at least as effective as verapamil. The cobalt-polypyridyl complex of Formula (IV) advantageously inhibits P-glycoprotein functional activity in A549 taxol-resistant lung cancer cells.

Example 7

Effects of Cobalt-Polypyridyl Complex of Formula (IV) in P-Glycoprotein (P-Gp) Inhibition Activity of P-gp ATPase in response to cobalt-polypyridyl complex of Formula (IV) or verapamil was determined by Pgp-Glo assay system (Promega, Madison, Wis.). According to the manufacturer's instruction, the inhibitory effect of 0.5 μM, 1 μM and 2 μM of cobalt-polypyridyl complex of Formula (IV) on the activity of P-gp ATPase was measured in the presence of 200 μM verapamil (as a positive stimulator). The luminescence of the sample reflects the ATP level in the sample, which is negatively correlated with the activity of P-gp ATPase and was recorded using the SpectraMax Paradigm Multi-Mode Microplate Reader (Molecular Devices). DMSO-treated activities are expressed as the percentage of basal activity. By comparing basal activity to test compound-treated activities, the compounds can be ranked as stimulating, inhibiting, or having no effect on basal P-gp ATPase activity.

Figure 6:
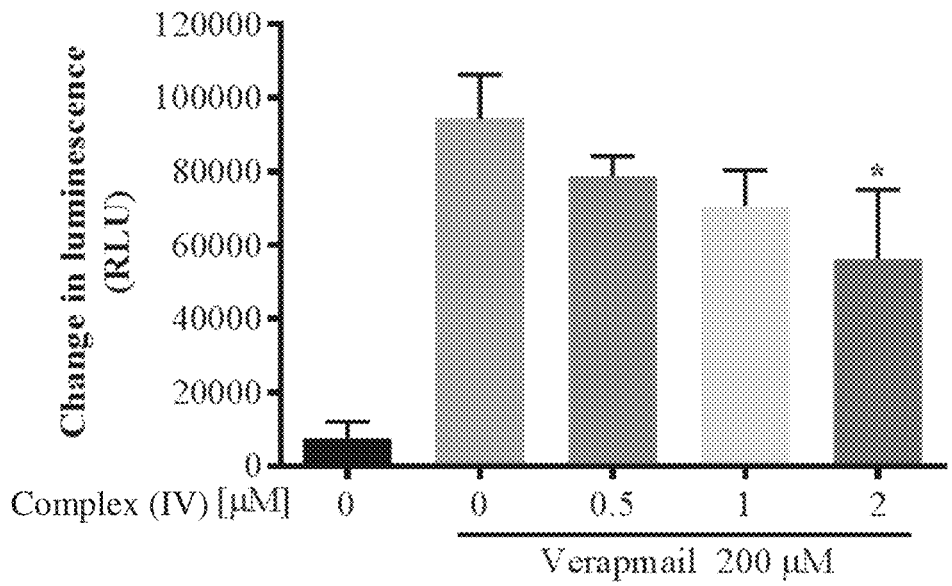
FIG. 6 is a diagram showing the effects of the cobalt-polypyridyl complex of Formula (IV) on P-glycoprotein (P-gp) via a direct P-gp Glo-activity assay. The diagram shows the change in luminescence signal of the activated P-gp activity after subjecting P-glycoprotein ATPase with the cobalt-polypyridyl complex of Formula (IV) with 0 μM, 0.5 μM, 1 μM and 2 μM and in the presence of 200 μM verapamil (200 μM).

As shown in FIG. 6, P-gp Glo-activity assay validated that cobalt-polypyridyl complex of Formula (IV) is capable of directly binding and suppressing the activated form of P-gp in a dose-dependent manner, indicating that cobalt-polypyridyl complex of Formula (IV) is a direct P-gp inhibitor.

The invention claimed is:
1. A method for inhibiting the expression and/or functional activity of an ABC transporter protein in a subject suffering from a disorder associated with an overexpression of the ABC transporter protein, comprising the step of administering an effective amount of a cobalt-polypyridyl complex of Formula (II) to the subject:

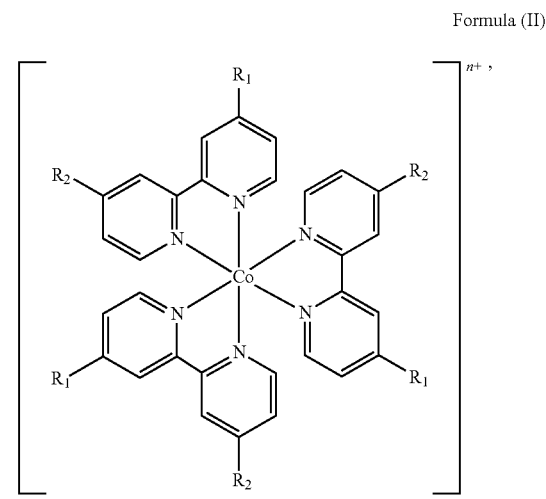

Formula (II)

wherein $R_1$ and $R_2$ are identical and selected from, —$CH_3$, —$C_9H_{19}$ or —$OCH_3$; wherein n is 2 or 3; and wherein the disorder is selected from the group consisting of breast cancer, lung cancer, and colon cancer.

2. The method of claim 1, wherein the ABC transporter protein is P-glycoprotein.

3. The method of claim 1, wherein the disorder is multidrug-resistant cancer.

4. The method of claim 3, wherein the subject is a human and the multidrug-resistant cancer is ABC-protein-dependent against at least taxol.

5. The method of claim 1, wherein the subject is a human.

6. The method of claim 1, wherein the cobalt-polypyridyl complex comprises a structure selected from Formula (III), Formula (IV) or Formula (V):

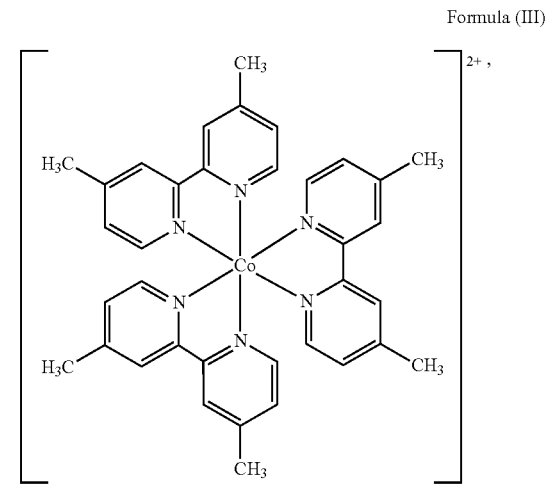

Formula (III)

Formula (IV)

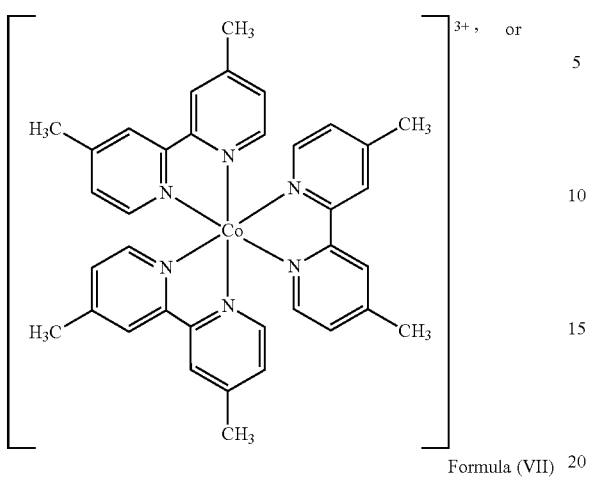

Formula (VII)

7. The method of claim 1, wherein the cobalt-polypyridyl complex comprises a structure of Formula (IV):

Formula (IV)

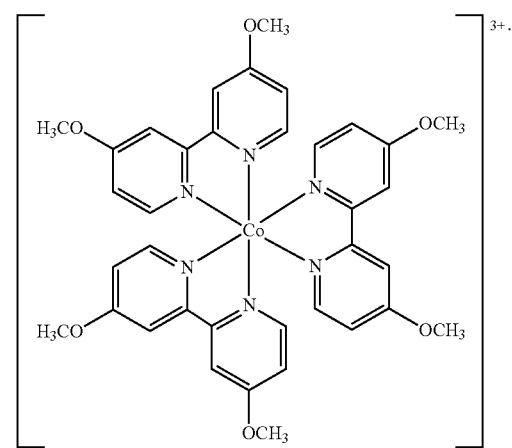

8. The method of claim 1, wherein the cobalt-polypyridyl complex is administered in combination with:
  (ii) an effective amount of at least one chemotherapeutic compound, which chemotherapeutic compound is a compound selected from the group consisting of a topoisomerase-II inhibitor, an anthracycline, a coordination complex of platinum, a taxane, a protein kinase inhibitor, a vinca alkaloid or derivative thereof, a topoisomerase-I inhibitor and a nucleotide analog or precursor analog;
  (ii) radiotherapy, and/or
  (iii) immunotherapy.

9. A method for inhibiting the expression and/or functional activity of an ABC transporter protein in cells by contacting the cells with an effective amount of a cobalt-polypyridyl complex, wherein the cobalt-polypyridyl complex comprises a structure of Formula (II):

Formula (II)

wherein $R_1$ and $R_2$ are identical and selected, —$CH_3$, —$C_9H_{19}$ or —$OCH_3$; wherein n is 2 or 3, and wherein the cells are cancer cells and are selected from the group consisting of breast cancer cells, lung cancer cells, and colon cancer cells.

10. The method of claim 9, wherein the ABC transporter protein is P-glycoprotein.

11. The method of claim 9, wherein the cells are contacted with of from about 0.5 μM to about 10 μM of said cobalt-polypyridyl complex.

12. The method of claim 9, wherein the cells are multidrug-resistant cells with an overexpression of the ABC transporter protein.

13. The method of claim 9, wherein the cancer cells are multidrug-resistant cancer cells against at least taxol.

14. The method of claim 9, wherein the cobalt-polypyridyl complex comprises a structure selected from Formula (III), Formula (IV) or Formula (V):

Formula (III)
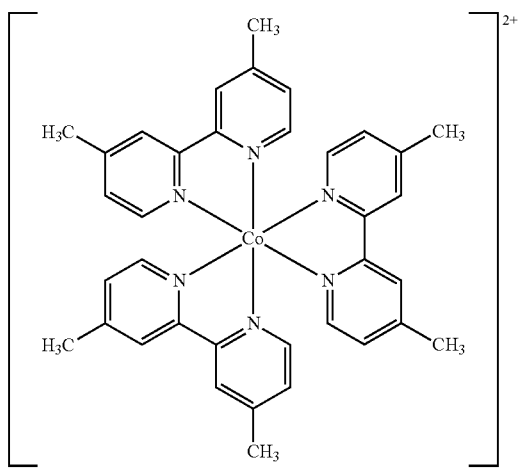
Formula (VII)
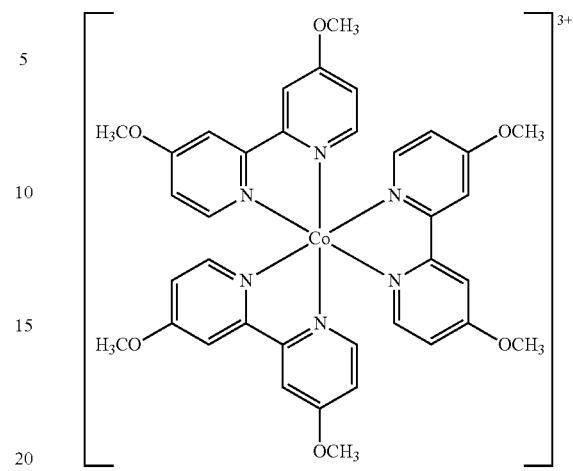
15. The method of claim 9, wherein the cobalt-polypyridyl complex comprises a structure of Formula (IV):
Formula (IV)
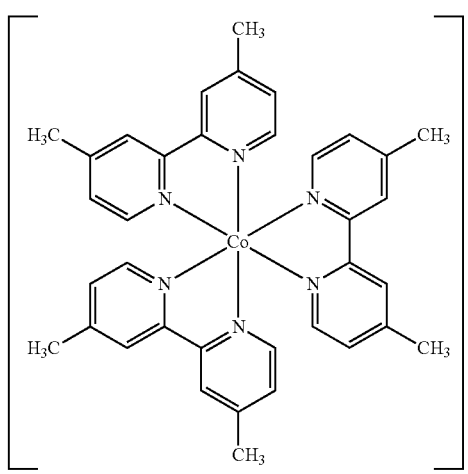
, or
Formula (IV)
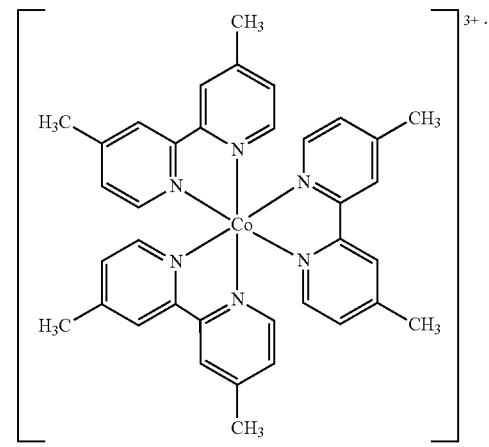
.
* * * * *